United States Patent
Shimizukawa

(10) Patent No.: US 12,186,117 B2
(45) Date of Patent: Jan. 7, 2025

(54) RADIOGRAPHIC IMAGE DETECTOR, METHOD FOR OPERATING RADIOGRAPHIC IMAGE DETECTOR, PROGRAM FOR OPERATING RADIOGRAPHIC IMAGE DETECTOR, AND RADIOGRAPHY SYSTEM

(71) Applicant: FUJIFILM CORPORATION, Tokyo (JP)

(72) Inventor: Sho Shimizukawa, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 291 days.

(21) Appl. No.: 18/045,821

(22) Filed: Oct. 11, 2022

(65) Prior Publication Data
US 2023/0165550 A1 Jun. 1, 2023

(30) Foreign Application Priority Data
Nov. 26, 2021 (JP) .................. 2021-192530

(51) Int. Cl.
*A61B 6/42* (2024.01)
*A61B 6/00* (2024.01)
*G01T 1/20* (2006.01)
*A61B 6/46* (2024.01)

(52) U.S. Cl.
CPC ............ *A61B 6/4208* (2013.01); *A61B 6/542* (2013.01); *A61B 6/465* (2013.01); *G01T 1/20181* (2020.05)

(58) Field of Classification Search
CPC ........ A61B 6/4208; A61B 6/542; A61B 6/465
See application file for complete search history.

(56) References Cited

U.S. PATENT DOCUMENTS

| | | | |
|---|---|---|---|
| 2005/0088566 A1* | 4/2005 | Tamura | H04N 25/626 348/E5.081 |
| 2014/0219422 A1 | 8/2014 | Nishino et al. | |
| 2016/0354051 A1* | 12/2016 | Enomoto | A61B 6/4241 |
| 2020/0066394 A1* | 2/2020 | Toyoda | G16H 10/60 |

FOREIGN PATENT DOCUMENTS

JP 2015-198939 A 11/2015

* cited by examiner

*Primary Examiner* — Chih-Cheng Kao
(74) *Attorney, Agent, or Firm* — SOLARIS Intellectual Property Group, PLLC

(57) ABSTRACT

An electronic cassette has a detection panel in which pixels accumulating charge corresponding to radiation emitted from a radiation source are arranged. A CPU of the electronic cassette transmits and receives a synchronizing signal to and from a radiation source control device. The CPU of the electronic cassette receives a setting notification signal indicating that irradiation conditions have been set from a console. After receiving the setting notification signal, the CPU of the electronic cassette directs the detection panel to start a charge reading operation. The CPU of the electronic cassette transmits an imaging preparation completion signal to the console after a predetermined number of charge reading operations are completed to notify that the predetermined number of charge reading operations have been completed.

9 Claims, 18 Drawing Sheets

Figure 1:
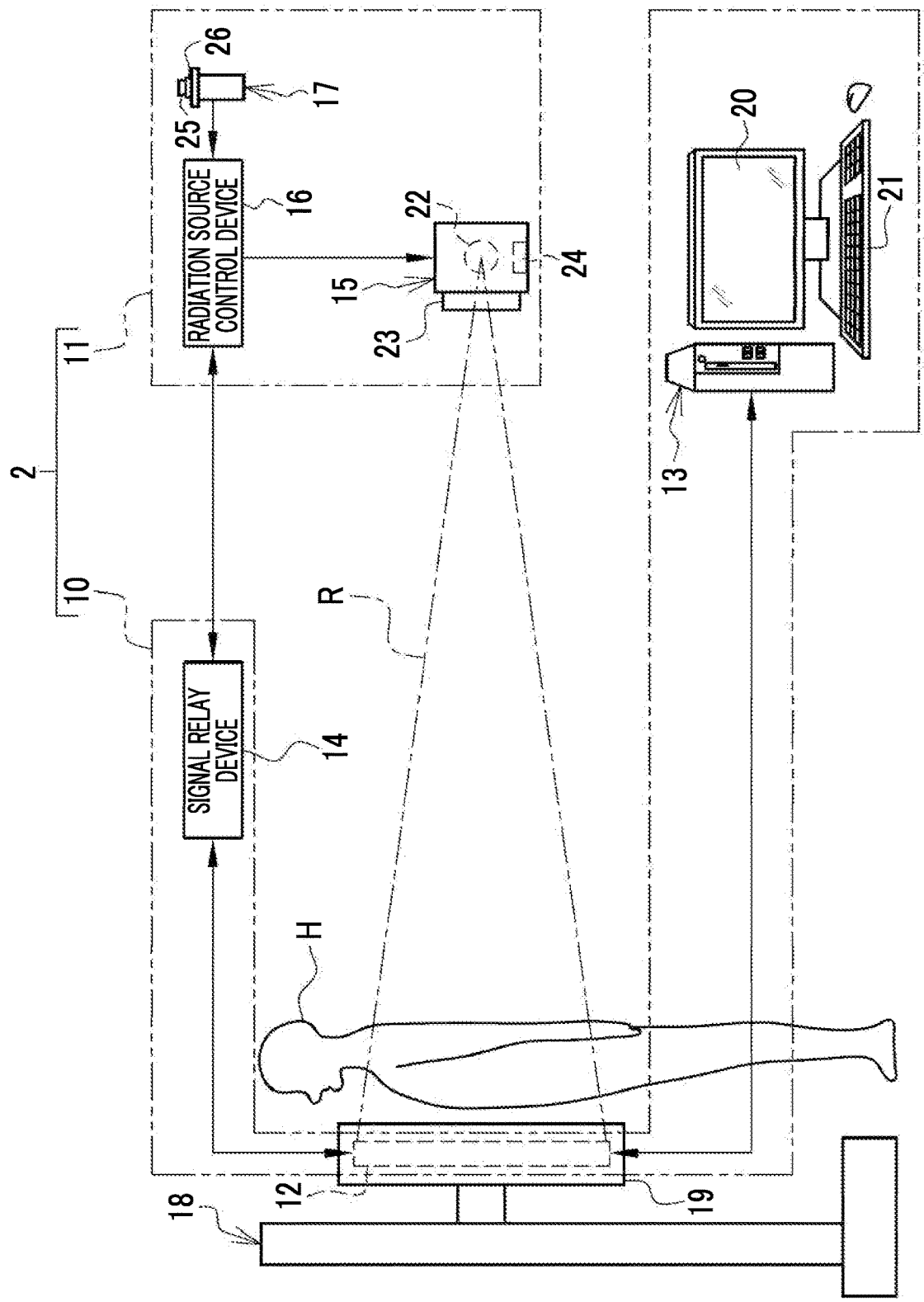

<COMPARATIVE EXAMPLE>

RADIOGRAPHIC IMAGE DETECTOR, METHOD FOR OPERATING RADIOGRAPHIC IMAGE DETECTOR, PROGRAM FOR OPERATING RADIOGRAPHIC IMAGE DETECTOR, AND RADIOGRAPHY SYSTEM

CROSS-REFERENCE TO RELATED APPLICATIONS

The present application claims priority under 35 U.S.C. § 119 to Japanese Patent Application No. 2021-192530, filed on Nov. 26, 2021. The above application is hereby expressly incorporated by reference, in its entirety, into the present application.

BACKGROUND

1. Technical Field

The technology of the present disclosure relates to a radiographic image detector, a method for operating a radiographic image detector, a program for operating a radiographic image detector, and a radiography system.

2. Description of the Related Art

A radiographic image detector is known that has a detection panel in which pixels accumulating charge corresponding to radiation emitted from a radiation source are arranged. The detection panel is also called a flat panel detector (FPD). In this radiographic image detector, before charge corresponding to radiation is accumulated, a charge reading operation of reading unnecessary charge from the pixels is repeatedly performed a predetermined number of times. The unnecessary charge is dark charge generated regardless of whether or not radiation is emitted and residual charge (so-called residual image) caused by previous radiography.

In addition, in the radiographic image detector having the detection panel, it is necessary to synchronize the operation of the radiation source. As a synchronization method, there is a method in which a radiation source control device that controls the operation of a radiation source and a radiographic image detector are connected to each other and a synchronizing signal is transmitted and received between the radiation source control device and the radiographic image detector.

For example, JP2015-198939A discloses an aspect in which a synchronizing signal is transmitted and received between a radiation source control device and a radiographic image detector through an imaging control device. In JP2015-198939A, in a case in which an operator, such as a radiology technician, sets irradiation conditions of radiation (a tube voltage, a tube current, and an irradiation time) in the imaging control device, a detection panel starts a charge reading operation.

SUMMARY

In the technique disclosed in JP2015-198939A, in a case in which the operator instructs a radiation source to start the emission of the radiation before a predetermined number of charge reading operations are completed, the radiation source starts the emission of the radiation after waiting for the completion of the predetermined number of charge reading operations. Therefore, the operator may feel uncomfortable due to a discrepancy between the instruction of the operator and the operation of the radiation source.

One embodiment according to the technology of the present disclosure is to provide a radiographic image detector, a method for operating a radiographic image detector, a program for operating a radiographic image detector, and a radiography system that can reduce a concern that an operator will feel discomfort.

According to an aspect of the present disclosure, there is provided a radiographic image detector having a detection panel in which pixels accumulating charge corresponding to radiation emitted from a radiation source are arranged. The radiographic image detector comprises a processor. The processor transmits and receives a synchronizing signal for synchronizing an operation of the radiation source to and from a radiation source control device which controls the operation of the radiation source, receives, from an imaging control device in which imaging-related information related to radiography is set, a setting notification signal indicating that the imaging-related information has been set, directs the detection panel to start a charge reading operation of reading the charge from the pixel after the setting notification signal is received, and notifies, after a predetermined number of charge reading operations are completed, that the predetermined number of charge reading operations have been completed.

Preferably, the radiographic image detector has a rectangular shape in a plan view and has a long side with a length greater than 431.8 mm.

Preferably, the radiation source control device receives an irradiation start command signal for instructing the radiation source to start the emission of the radiation and transmits an irradiation start command reception signal indicating that the irradiation start command signal has been received as the synchronizing signal, and the processor directs the detection panel to continue the charge reading operation until the irradiation start command reception signal is received from the radiation source control device even after the predetermined number of charge reading operations are completed.

Preferably, after receiving the irradiation start command reception signal from the radiation source control device, the processor directs the detection panel to start an accumulation operation of accumulating the charge in the pixel and transmits an irradiation permission signal for permitting the emission of the radiation to the radiation source control device.

Preferably, the imaging-related information includes at least one of a time for which the detection panel performs an accumulation operation of accumulating the charge in the pixel, irradiation conditions of the radiation, an imaging part of a subject, an imaging posture of the subject, or an imaging direction of the subject.

Preferably, the radiographic image detector has a function of detecting a start of the emission of the radiation without depending on the synchronizing signal.

According to another aspect of the present disclosure, there is provided a method for operating a radiographic image detector having a detection panel in which pixels accumulating charge corresponding to radiation emitted from a radiation source are arranged. The method comprises: transmitting and receiving a synchronizing signal for synchronizing an operation of the radiation source to and from a radiation source control device which controls the operation of the radiation source; receiving, from an imaging control device in which imaging-related information related to radiography is set, a setting notification signal indicating that the imaging-related information has been set; directing the detection panel to start a charge reading operation of reading the charge from the pixel after the setting notification signal is received; and notifying, after a predetermined number of charge reading operations are completed, that the predetermined number of charge reading operations have been completed.

According to yet another aspect of the present disclosure, there is provided a program for operating a radiographic image detector having a detection panel in which pixels accumulating charge corresponding to radiation emitted from a radiation source are arranged. The program causes a computer to execute a process comprising: transmitting and receiving a synchronizing signal for synchronizing an operation of the radiation source to and from a radiation source control device which controls the operation of the radiation source; receiving, from an imaging control device in which imaging-related information related to radiography is set, a setting notification signal indicating that the imaging-related information has been set; directing the detection panel to start a charge reading operation of reading the charge from the pixel after the setting notification signal is received; and notifying, after a predetermined number of charge reading operations are completed, that the predetermined number of charge reading operations have been completed.

According to still another aspect of the present disclosure, there is provided a radiography system comprising: a radiation source that emits radiation; a radiation source control device that controls an operation of the radiation source; a radiographic image detector that has a detection panel in which pixels accumulating charge corresponding to the radiation are arranged; and an imaging control device in which imaging-related information related to radiography is set. The radiographic image detector has a processor. The processor transmits and receives a synchronizing signal for synchronizing an operation of the radiation source to and from the radiation source control device, receives a setting notification signal indicating that the imaging-related information has been set from the imaging control device, directs the detection panel to start a charge reading operation of reading the charge from the pixel after the setting notification signal is received, and notifies, after a predetermined number of charge reading operations are completed, that the predetermined number of charge reading operations have been completed.

According to the technology of the present disclosure, it is possible to provide a radiographic image detector, a method for operating a radiographic image detector, a program for operating a radiographic image detector, and a radiography system that can reduce a concern that an operator will feel discomfort.

BRIEF DESCRIPTION I/F THE DRAWINGS

Figure 2:
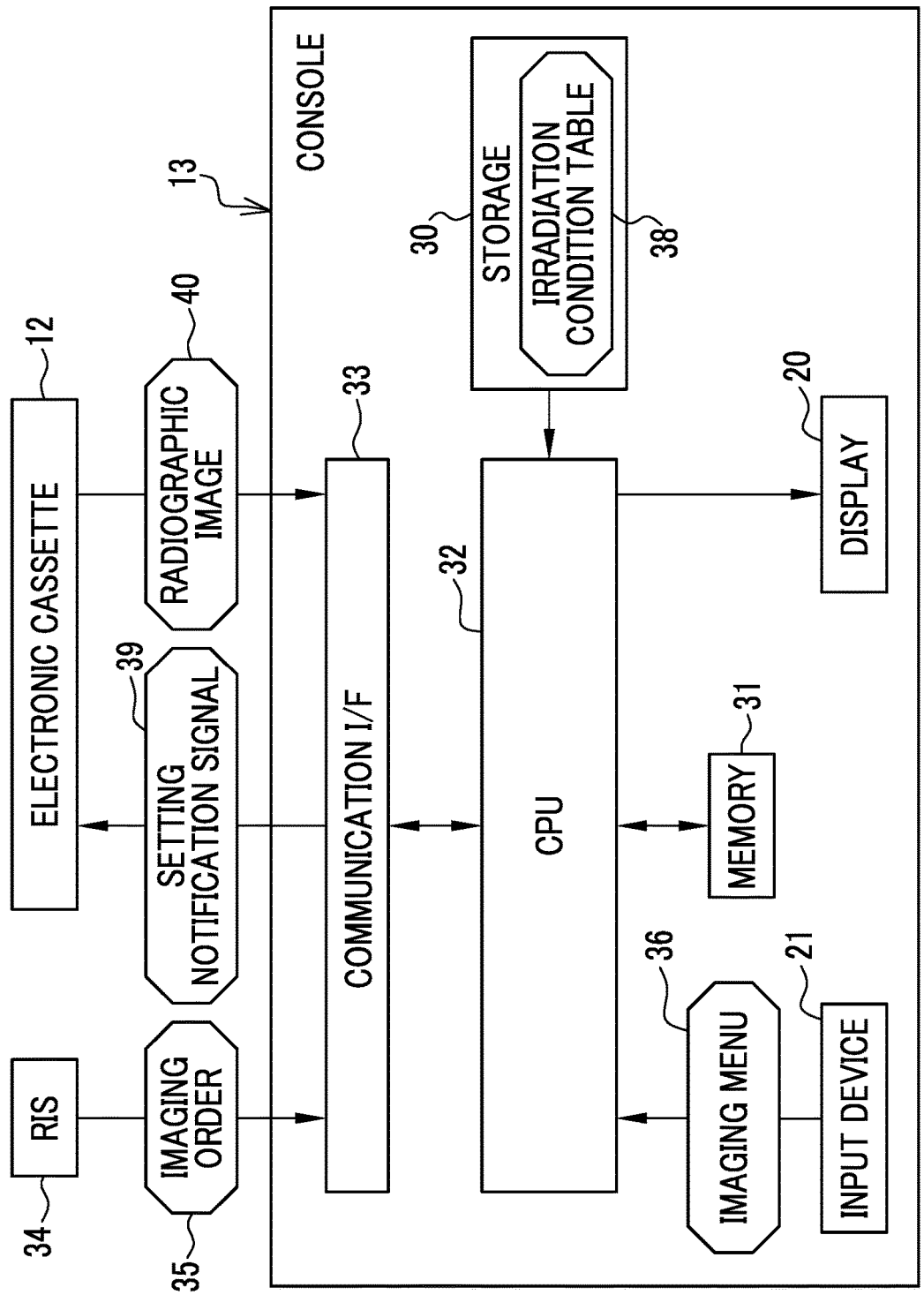
Figure 3:
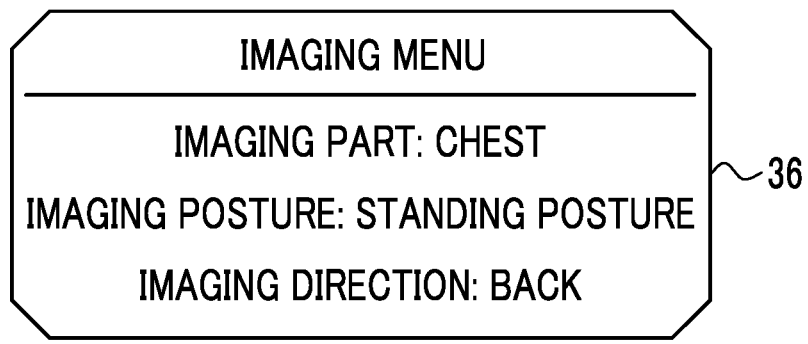
Figure 4:
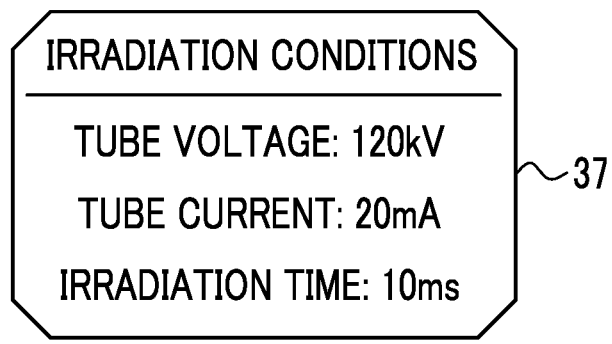
Figure 5:
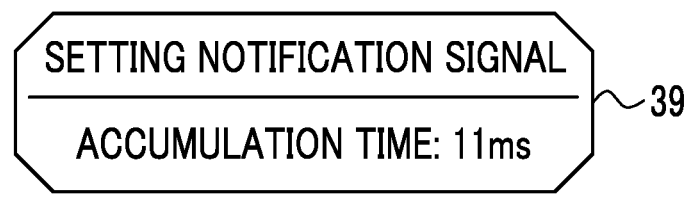
Figure 6:
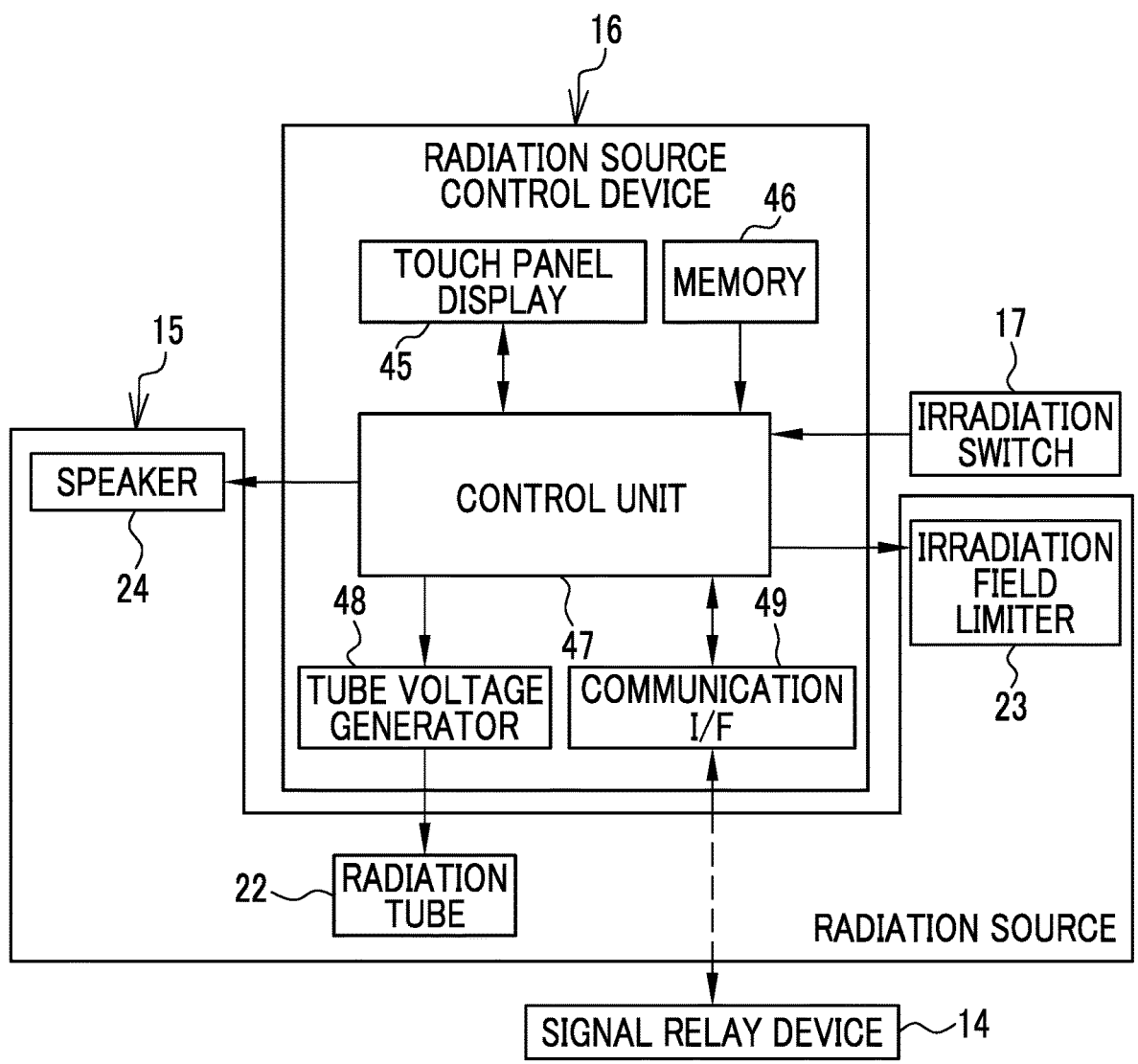
Figure 7:
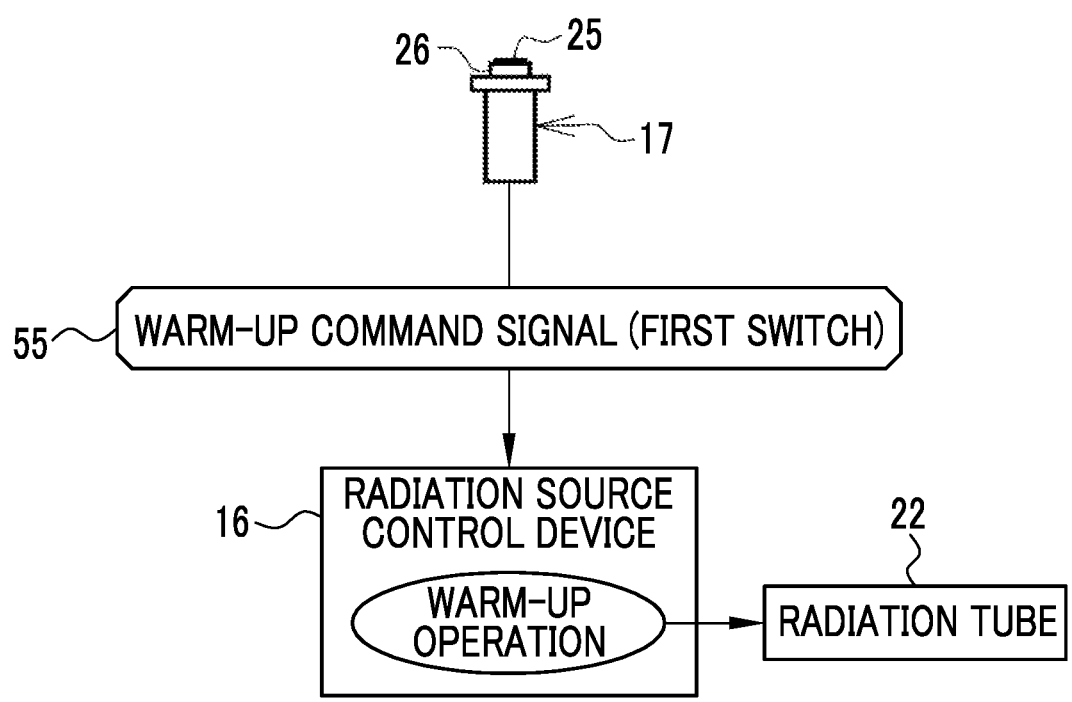
Figure 8:
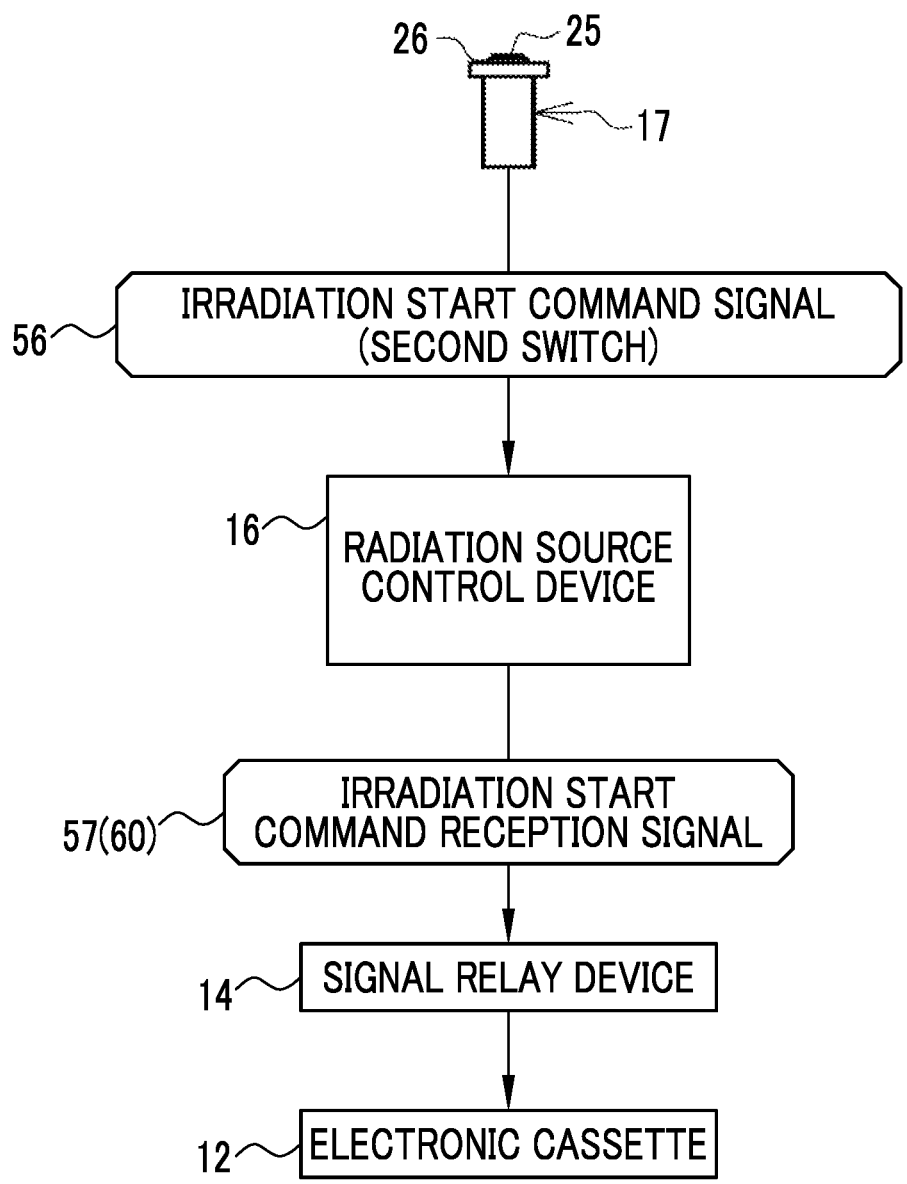
Figure 9:
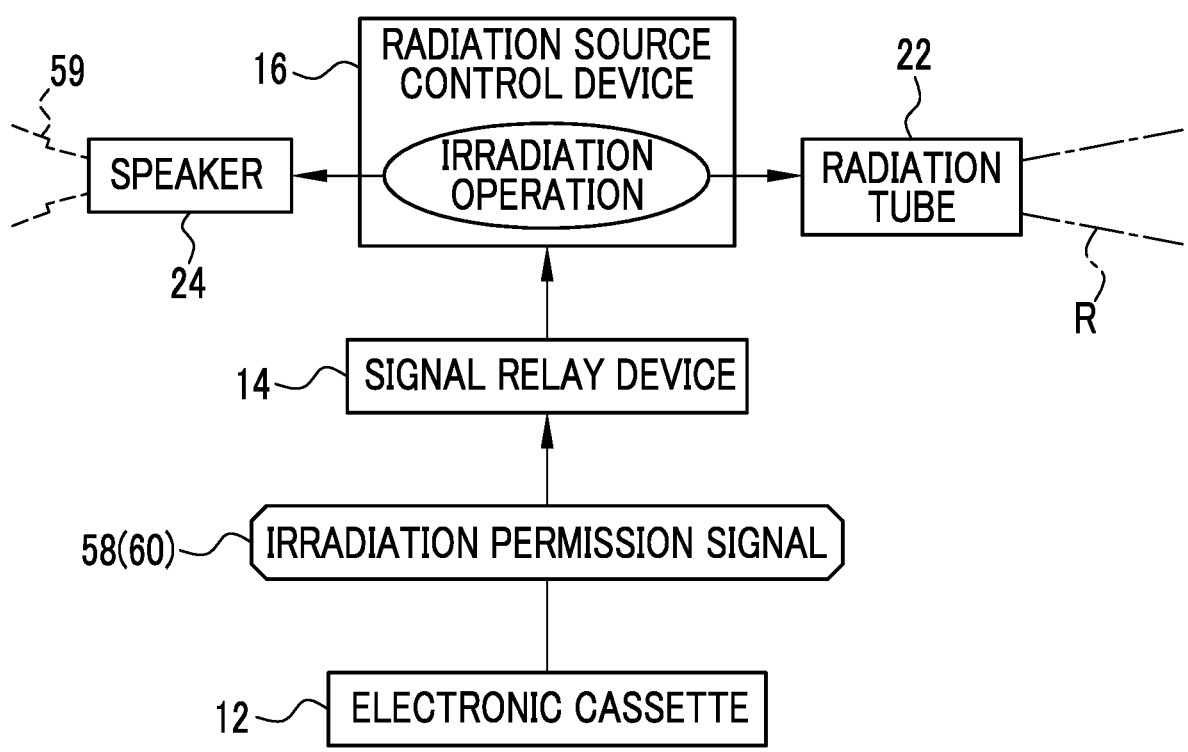
Figure 10:
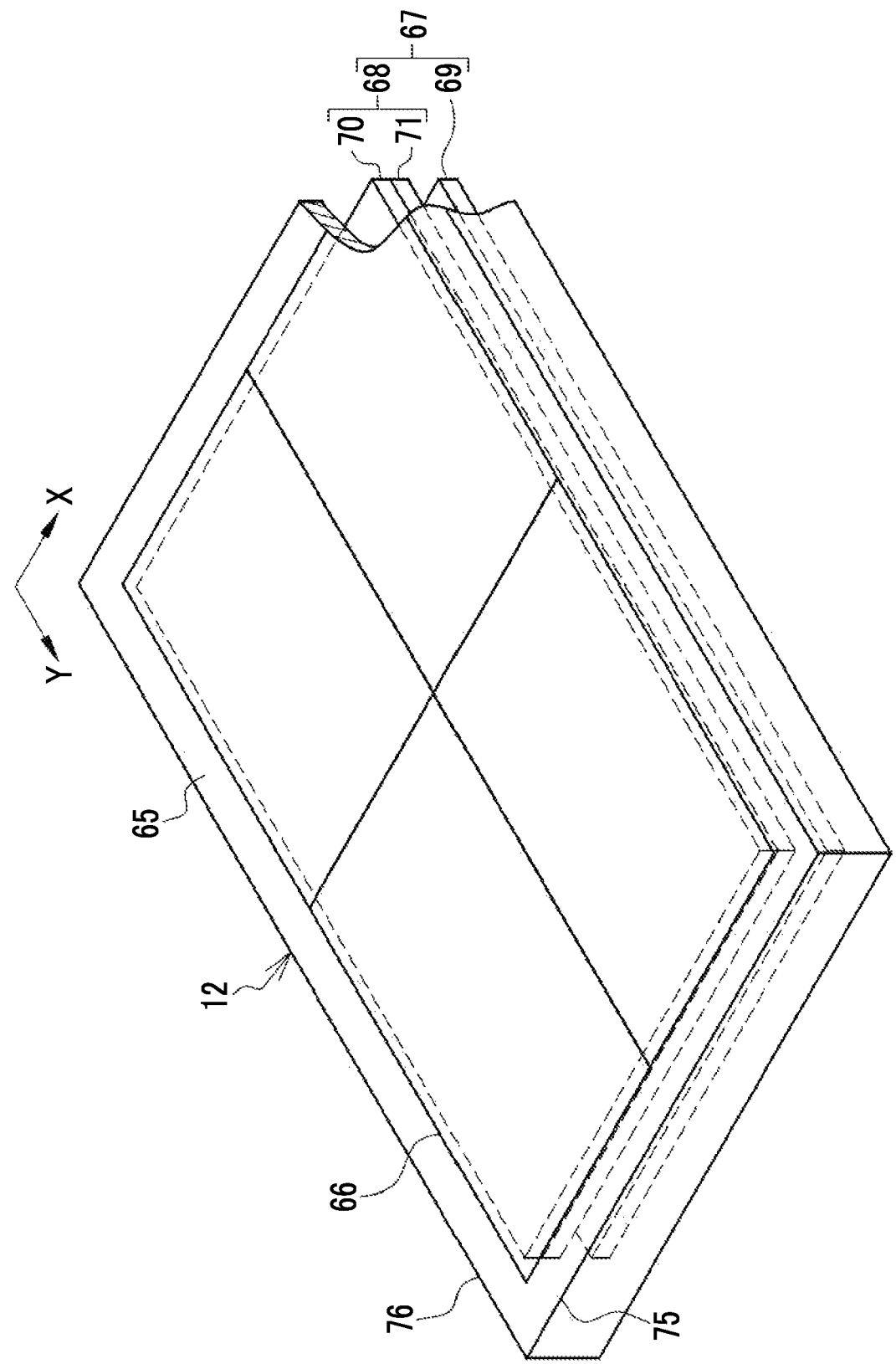
Figure 11:
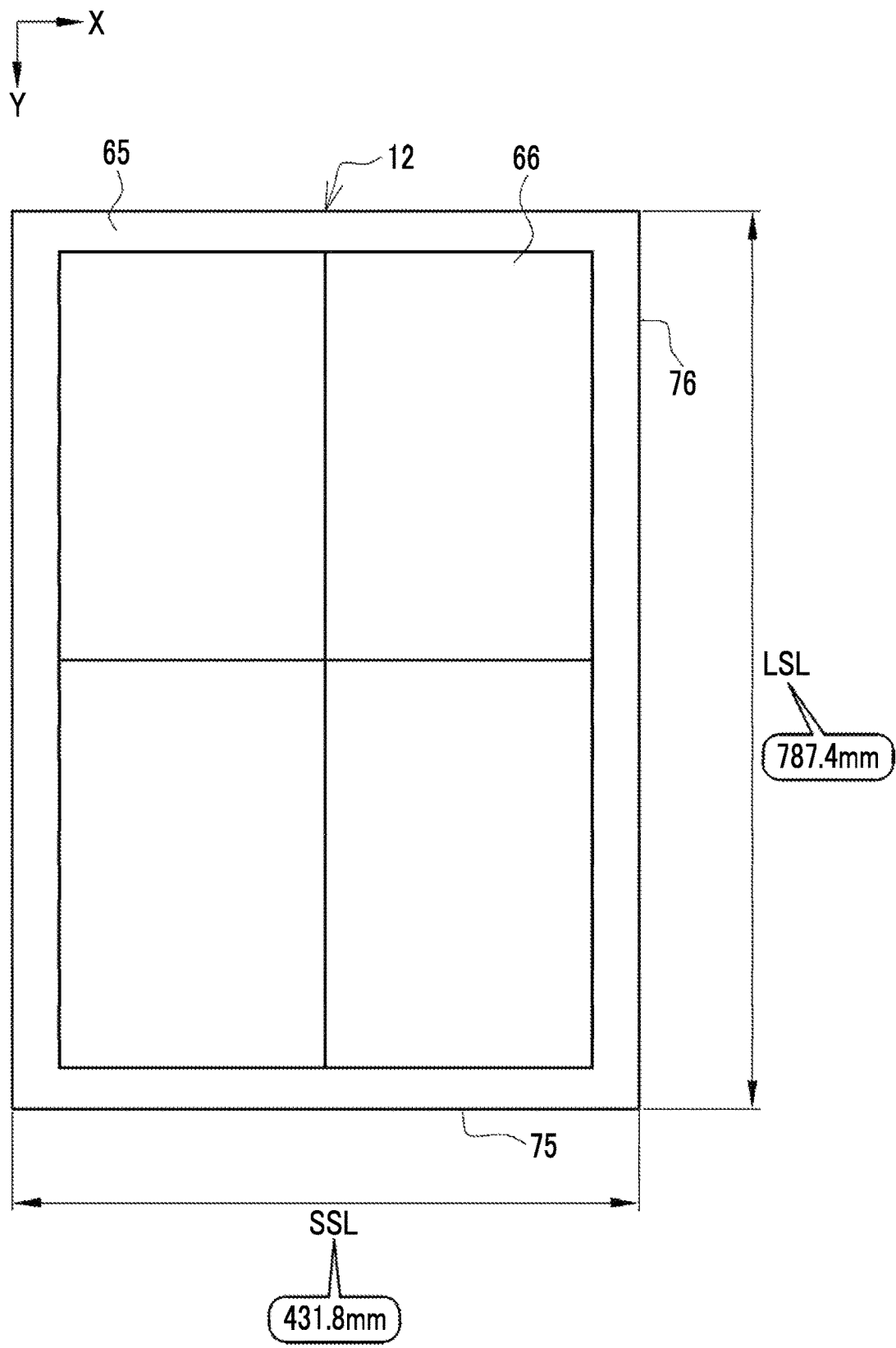
Figure 12:
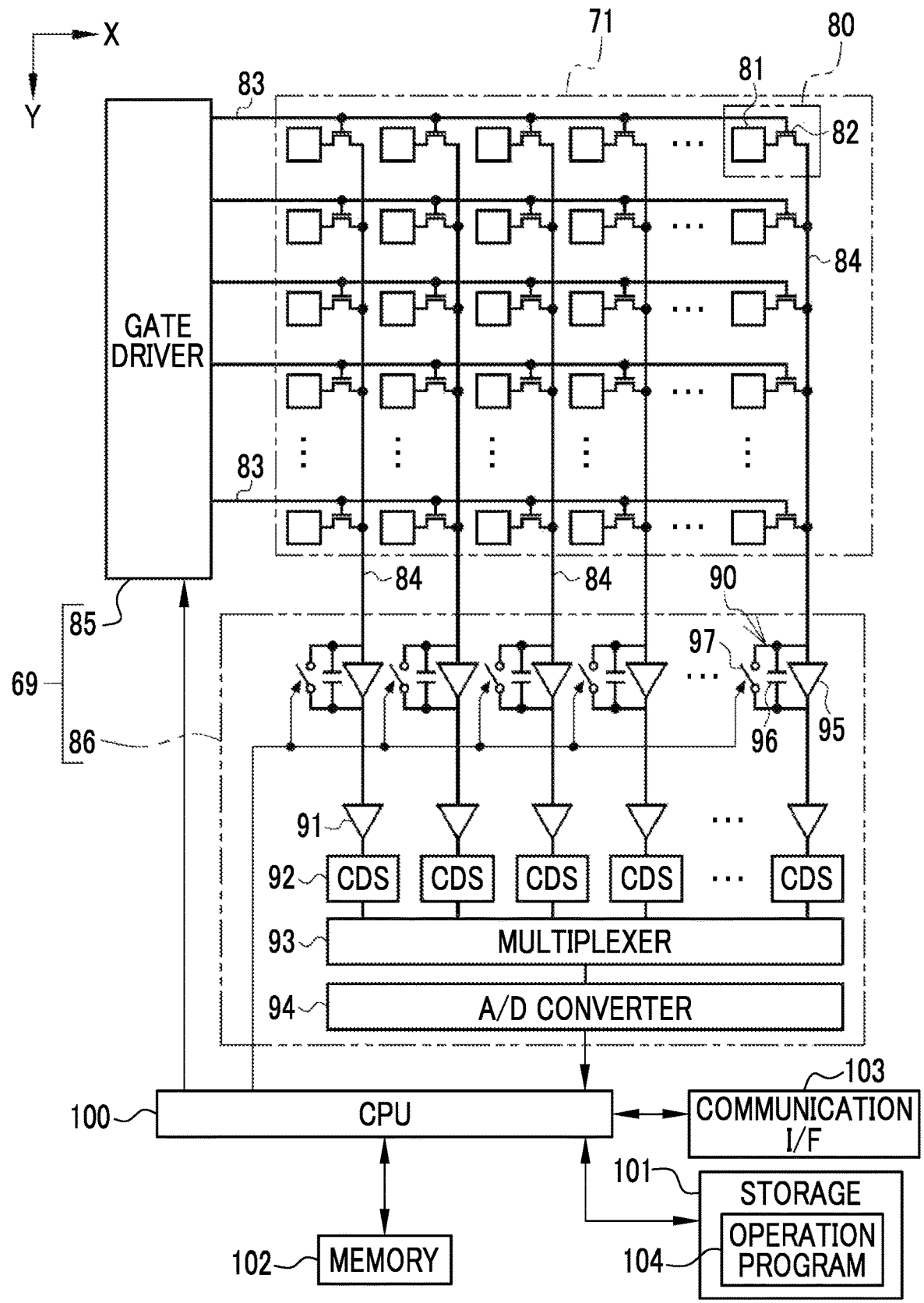
Figure 13:
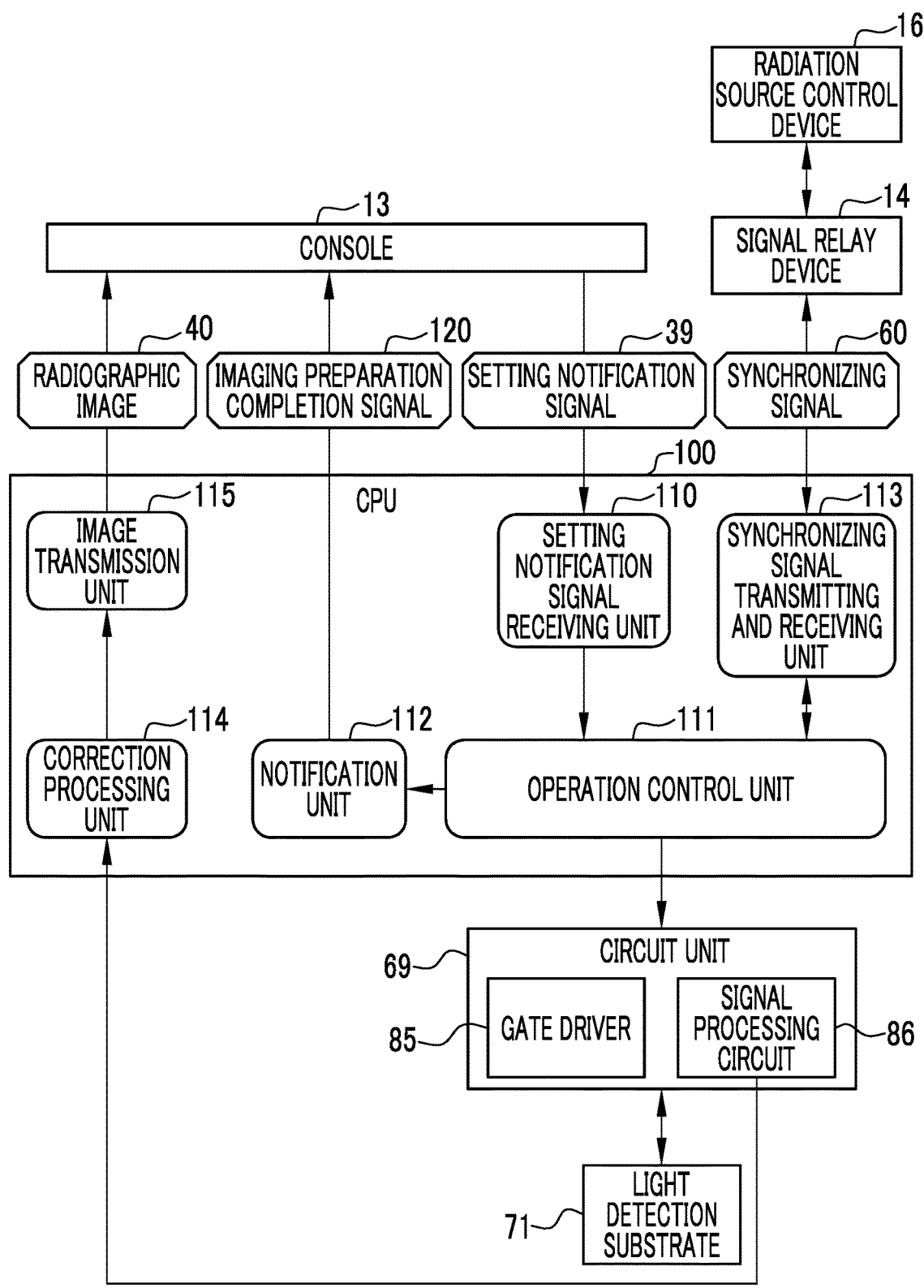
Figure 14:
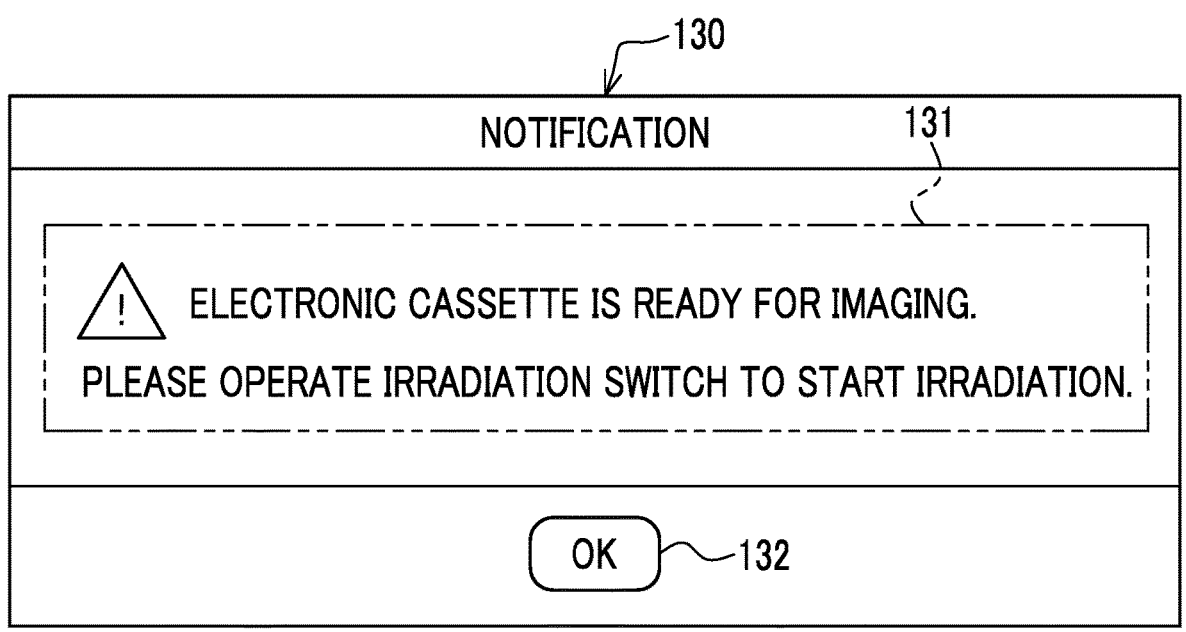
Figure 15:
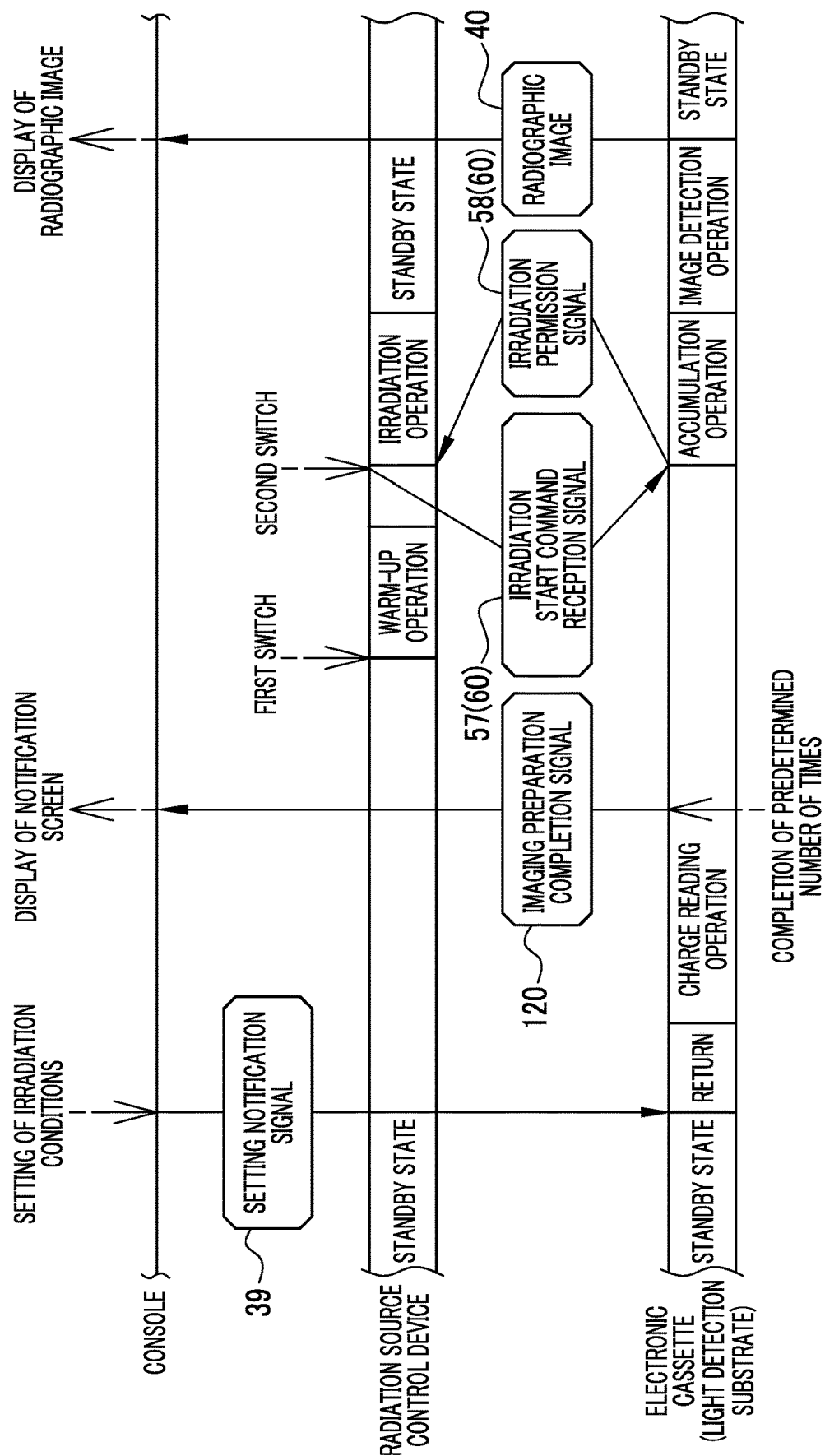
Figure 16:
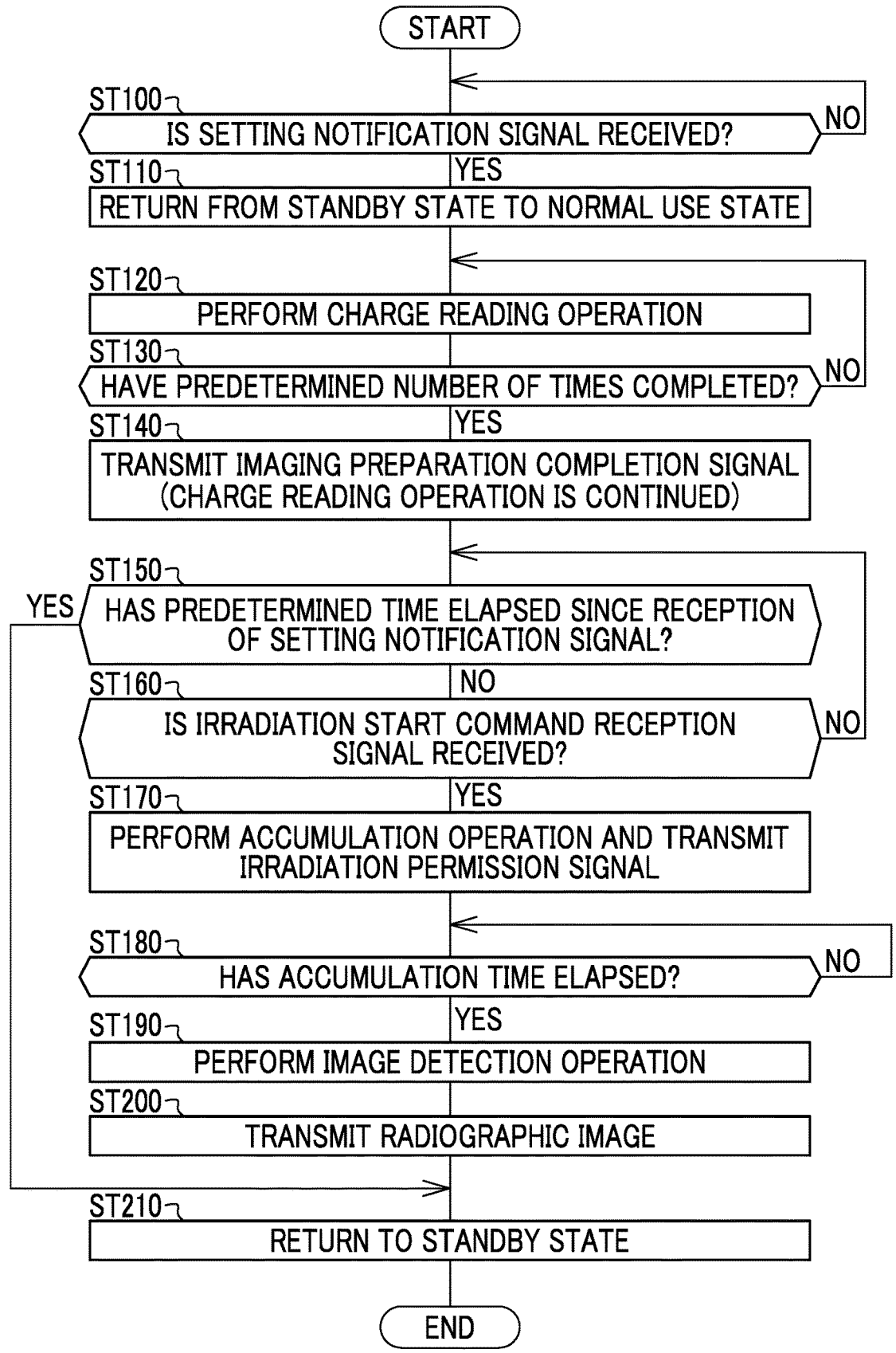
Figure 17:
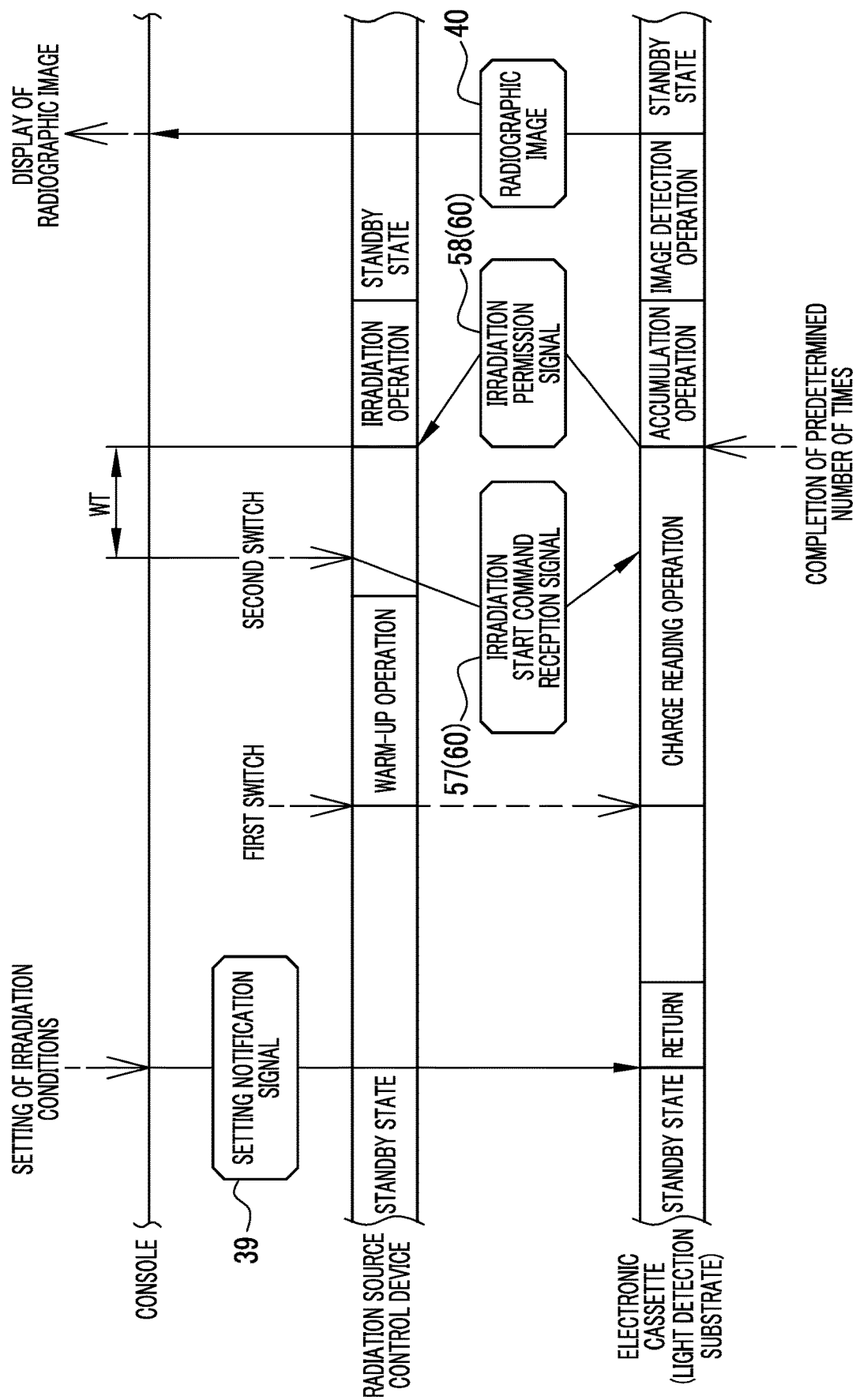
Figure 18:
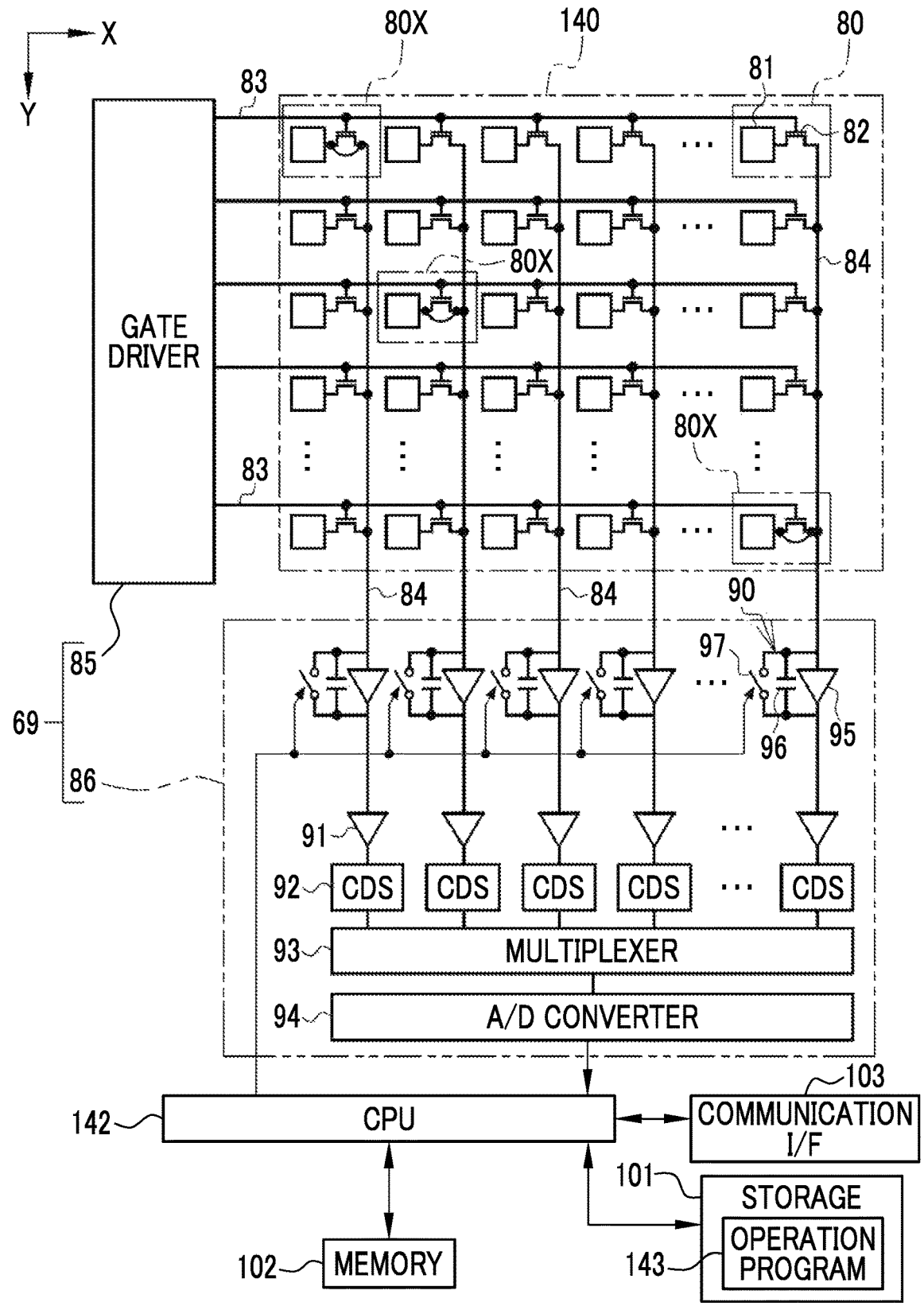
Figure 19:
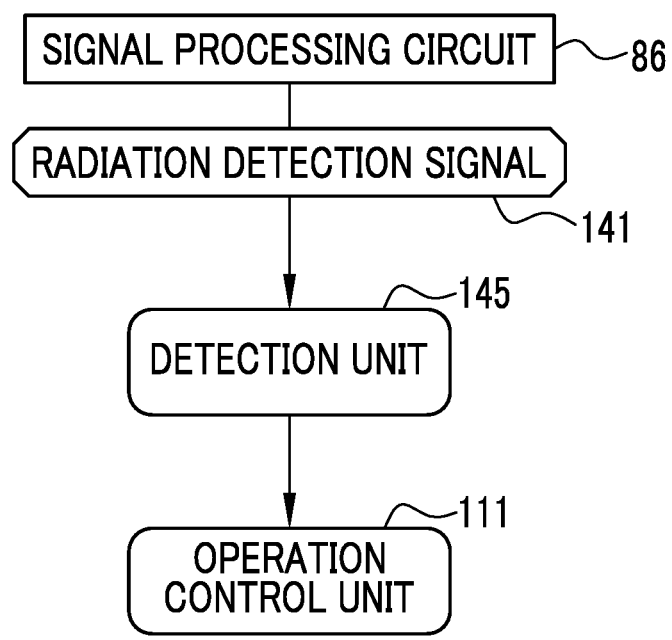
Figure 20:
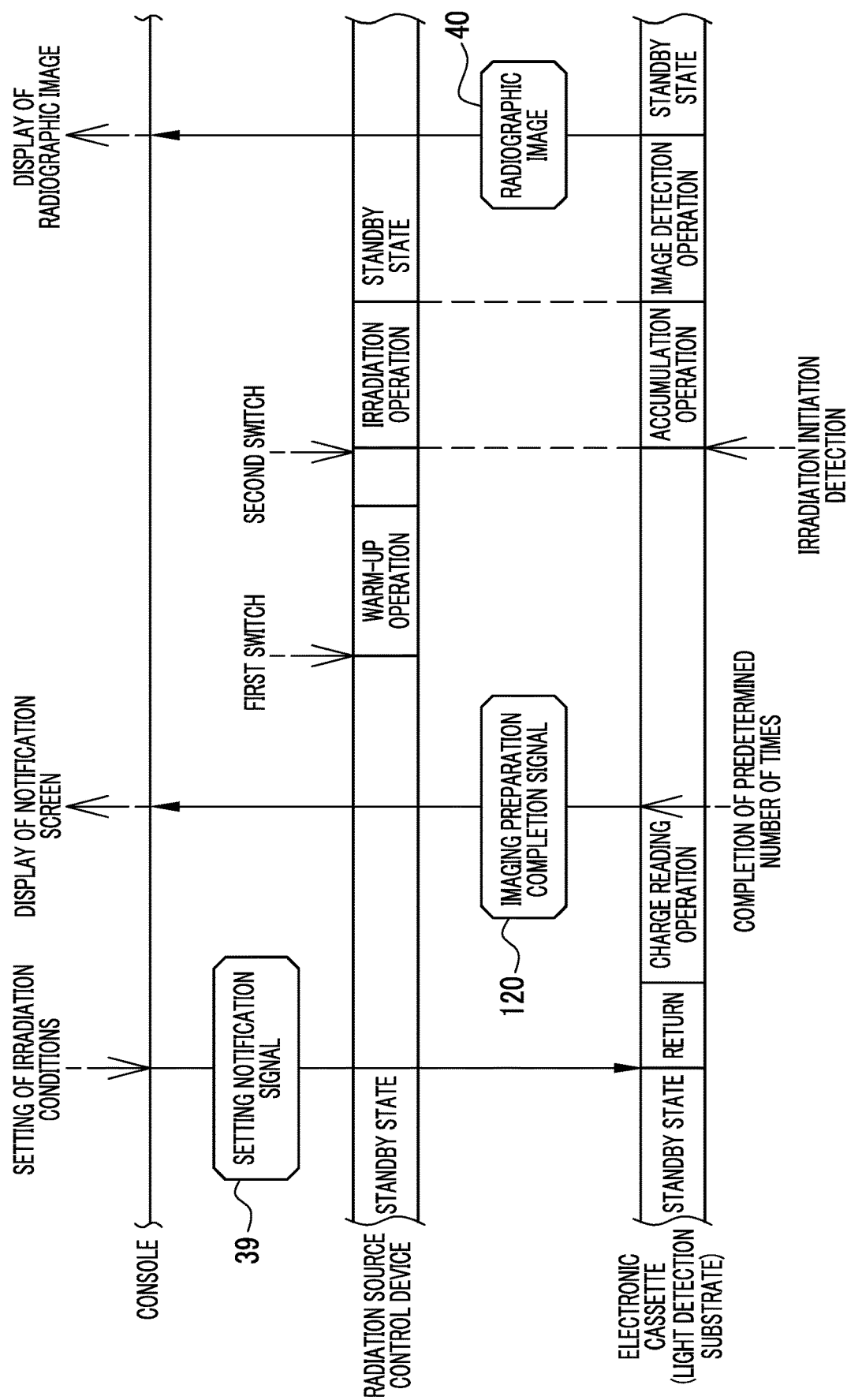

Exemplary embodiments according to the technique of the present disclosure will be described in detail based on the following figures, wherein:

FIG. 1 is a diagram illustrating a radiography system;
FIG. 2 is a block diagram illustrating an internal configuration of a console;
FIG. 3 is a diagram illustrating an imaging menu;
FIG. 4 is a diagram illustrating irradiation conditions;
FIG. 5 is a diagram illustrating a setting notification signal;
FIG. 6 is a block diagram illustrating an internal configuration of a radiation source control device;
FIG. 7 is a diagram illustrating an operation of the radiation source control device in a case in which a first switch is turned on and a warm-up command signal is received;
FIG. 8 is a diagram illustrating an operation of the radiation source control device in a case in which a second switch is turned on and an irradiation start command signal is received;
FIG. 9 is a diagram illustrating an operation of the radiation source control device in a case in which an irradiation permission signal is received from an electronic cassette;
FIG. 10 is a perspective view illustrating the electronic cassette;
FIG. 11 is a plan view illustrating the electronic cassette;
FIG. 12 is a diagram illustrating a configuration of a circuit unit and a detection panel;
FIG. 13 is a block diagram illustrating a CPU of the electronic cassette;
FIG. 14 is a diagram illustrating a notification screen;
FIG. 15 is a timing chart illustrating a series of operations of the console, the radiation source control device, and the electronic cassette (detection panel) in one radiography operation;
FIG. 16 is a flowchart illustrating an operation procedure of the electronic cassette;
FIG. 17 is a timing chart illustrating a series of operations of a console, a radiation source control device, and an electronic cassette (detection panel) in one radiography operation according to a comparative example;
FIG. 18 is a diagram illustrating a configuration of a circuit unit and a detection panel according to a second embodiment;
FIG. 19 is a block diagram illustrating a portion of a CPU of an electronic cassette according to the second embodiment; and
FIG. 20 is a timing chart illustrating a series of operations of the console, the radiation source control device, and the electronic cassette (detection panel) in one radiography operation according to the second embodiment.

DETAILED DESCRIPTION

First Embodiment

For example, as illustrated in FIG. 1, a radiography system 2 is a system that performs radiography on a subject H using radiation R, such as X-rays or γ-rays, and is composed of a radiography apparatus 10 and a radiation generation device 11. The radiography apparatus 10 has an electronic cassette 12, a console 13, and a signal relay device 14. The radiation generation device 11 has a radiation source 15, a radiation source control device 16, and an irradiation switch 17.

The electronic cassette 12 is a portable radiographic image detector that outputs a radiographic image 40 (see FIG. 2) corresponding to the radiation R transmitted through the subject H. The electronic cassette 12 is connected to the console 13 and the signal relay device 14 wirelessly or in a wired manner such that it can communicate with the console 13 and the signal relay device 14. The electronic cassette 12 is accommodated in, for example, a holder 19 of an upright imaging stand 18 and is then used. In addition, the electronic cassette 12 can be removed from the holder 19, stood up against the subject H or inserted under the subject H lying on a bed in a hospital room, and then used. Further, a decubitus imaging table may be provided instead of or in addition to the upright imaging stand 18. Furthermore, the electronic cassette 12 is an example of a "radiographic image detector" according to the technology of the present disclosure.

The console 13 is, for example, a desktop personal computer and has a display 20 that displays various screens and an input device 21 that includes a keyboard, a mouse, and the like and receives operation instructions from an operator of the radiography system 2. The console 13 transmits various signals to the electronic cassette 12. In addition, the console 13 receives the radiographic image 40 from the electronic cassette 12. The console 13 displays the radiographic image 40 on the display 20. The console 13 is an example of an "imaging control device" according to the technology of the present disclosure. In addition, the console 13 may be a notebook personal computer or a tablet terminal.

The signal relay device 14 relays a synchronizing signal 60 (see FIG. 13) that is transmitted and received between the electronic cassette 12 and the radiation source control device 16. The signal relay device 14 performs the following process in a case in which the radiography apparatus 10 and the radiation generation device 11 are manufactured by different manufacturers and the electronic cassette 12 and the radiation source control device 16 are not compatible with each other. That is, the signal relay device 14 converts the synchronizing signal 60 from the electronic cassette 12 into a synchronizing signal 60 suitable for the radiation source control device 16 and then transmits the synchronizing signal 60 to the radiation source control device 16. Further, the signal relay device 14 converts the synchronizing signal 60 from the radiation source control device 16 into a synchronizing signal 60 suitable for the electronic cassette 12 and then transmits the synchronizing signal 60 to the electronic cassette 12. Furthermore, in a case in which the electronic cassette 12 and the radiation source control device 16 are compatible with each other, the signal relay device 14 does not convert the synchronizing signal 60, and the synchronizing signal 60 from a transmission source flows to a reception destination without any change. Alternatively, in a case in which the electronic cassette 12 and the radiation source control device 16 are compatible with each other, the signal relay device 14 may not be provided.

The radiation source 15 has a radiation tube 22, an irradiation field limiter 23, and a speaker 24. The radiation tube 22 is provided with, for example, a filament, a target, and a grid electrode (none of which are illustrated). A voltage is applied between the filament, which is a cathode, and the target, which is an anode. The voltage applied between the filament and the target is called a tube voltage. The filament emits thermoelectrons corresponding to the applied tube voltage to the target. The target emits the radiation R by the collision of the thermoelectrons from the filament. The grid electrode is disposed between the filament and the target. The grid electrode changes the flow rate of the thermoelectrons from the filament to the target according to the applied voltage. The flow rate of the thermoelectrons from the filament to the target is called a tube current.

The irradiation field limiter 23 is also called a collimator and limits an irradiation field of the radiation R emitted from the radiation tube 22. For example, the irradiation field limiter 23 has a configuration in which four shielding plates made of lead or the like that shields the radiation R are disposed on each side of a quadrangle and a quadrangular emission opening for transmitting the radiation R is formed in a central portion. The irradiation field limiter 23 changes the position of each shielding plate to change the size of the emission opening, thereby changing the irradiation field of the radiation R. Immediately before the radiation R is emitted, the speaker 24 emits a beep sound 59 (see FIG. 9) for notifying the subject H that the radiation R is about to be emitted.

The radiation source 15 and the irradiation switch 17 are connected to the radiation source control device 16. The radiation source control device 16 controls the operation of the radiation source 15 in response to various command signals from the irradiation switch 17. The irradiation switch 17 is operated in a case in which the operator instructs the radiation source 15 to start the emission of the radiation R. The irradiation switch 17 is a two-stage push type having a first switch 25 and a second switch 26.

For example, as illustrated in FIG. 2, the console 13 comprises a storage 30, a memory 31, a central processing unit (CPU) 32, and a communication interface (I/F) 33 in addition to the display 20 and the input device 21. The display 20, the input device 21, the storage 30, the memory 31, the CPU 32, and the communication I/F 33 are connected to each other through a bus line (not illustrated).

The storage 30 is a hard disk drive that is provided in the computer constituting the console 13 or is connected to the computer through a cable or a network. The storage 30 stores, for example, a control program, such as an operating system, various application programs, and various kinds of data associated with these programs. In addition, a solid state drive may be used instead of the hard disk drive.

The memory 31 is a work memory used by the CPU 32 to perform processes. The CPU 32 loads the program stored in the storage 30 to the memory 31 and performs a process corresponding to the program. Therefore, the CPU 32 controls the overall operation of each unit of the computer. In addition, the memory 31 may be provided in the CPU 32. The communication I/F 33 controls the transmission of various kinds of information to the electronic cassette 12 or an external device such as a radiology information system (RIS) 34.

The CPU 32 receives an imaging order 35 from the RIS 34 through the communication I/F 33. For example, subject identification data (ID) for identifying the subject H and an imaging procedure instruction from a doctor of a clinical department that has issued the imaging order 35 are registered in the imaging order 35. The CPU 32 displays the imaging order 35 on the display 20 according to the operation of the operator using the input device 21. The operator checks the content of the imaging order 35 through the display 20.

The CPU 32 displays a plurality of types of imaging menus 36 on the display 20 to be selectable. For example, as illustrated in FIG. 3, the imaging menu 36 defines an imaging procedure in which the imaging part of the subject H, the imaging posture of the subject H, and the imaging direction of the subject H, such as "a chest, a standing posture, and a back", form one set. Examples of the imaging part include the head, the neck, the abdomen, the waist, the shoulder, the elbow, the hand, the knee, the ankle in addition to the chest. Examples of the imaging posture include a decubitus posture and a sitting posture in addition to the standing posture. Examples of the imaging direction include the front and the side in addition to the back. The operator operates the input device 21 to select one imaging menu 36 that is matched with the imaging procedure designated by the imaging order 35 from the plurality of types of imaging menus 36. Then, the CPU 32 receives the imaging menu 36. The CPU 32 reads irradiation conditions 37 (see FIG. 4) corresponding to the received imaging menu 36 from an irradiation condition table 38 stored in the storage 30. The CPU 32 displays the read irradiation conditions 37 on the display 20. The irradiation conditions 37 corresponding to various types of imaging menus 36 are registered in the irradiation condition table 38. For example, as illustrated in FIG. 4, the irradiation conditions 37 are a set of the tube voltage and the tube current applied to the radiation tube 22 and the irradiation time of the radiation R. Instead of the tube current and the irradiation time, a tube current-irradiation time product may be used as the irradiation condition 37. The irradiation conditions 37 are an example of "imaging-related information" according to the technology of the present disclosure.

In a case in which the imaging menu 36 is selected by the operator and the irradiation conditions 37 corresponding to the imaging menu 36 are set, the CPU 32 transmits a setting notification signal 39 indicating that the irradiation conditions 37 have been set to the electronic cassette 12 through the communication I/F 33. For example, as illustrated in FIG. 5, the setting notification signal 39 includes a time (hereinafter, referred to as an accumulation time) for which a light detection substrate 71 of a detection panel 68 (see FIG. 10) performs an accumulation operation which will be described below. The accumulation time is the time obtained by adding the time when the synchronizing signal 60 (see FIG. 13) is transmitted and received between the electronic cassette 12 and the radiation source control device 16 to the irradiation time of the irradiation condition 37. Further, in addition to or instead of the accumulation time, at least one of the irradiation time, the tube voltage, or the tube current may be included in the setting notification signal 39.

The CPU 32 receives the radiographic image 40 from the electronic cassette 12 through the communication I/F 33. After performing various types of image processing on the radiographic image 40, the CPU 32 displays the radiographic image 40 on the display 20 such that the operator views the radiographic image 40.

For example, as illustrated in FIG. 6, the radiation source control device 16 comprises a touch panel display 45, a memory 46, a control unit 47, a tube voltage generator 48, and a communication I/F 49. The touch panel display 45 displays various screens and receives operation instructions from the operator. Similarly to the irradiation condition table 38 for the console 13, a plurality of types of representative irradiation conditions 37 are registered in the memory 46. The control unit 47 reads the plurality of types of irradiation conditions 37 from the memory 46 and displays the read plurality types of irradiation conditions 37 on the touch panel display 45 so as to be selectable. The operator operates the touch panel display 45 to select irradiation conditions 37 matched with the irradiation conditions 37 set in the console 13 among the plurality of types of irradiation conditions 37. The control unit 47 sets the irradiation conditions 37 selected by the operator in the tube voltage generator 48. The tube voltage generator 48 boosts an input voltage with a transformer to generate a tube voltage. The tube voltage generated by the tube voltage generator 48 is supplied to the radiation tube 22 through a voltage cable (not illustrated). In addition, the irradiation conditions 37 can be corrected by operating the touch panel display 45 before being set in the tube voltage generator 48.

The control unit 47 transmits and receives the synchronizing signal 60 to and from the signal relay device 14 and thus the electronic cassette 12 through the communication I/F 49. Further, the control unit 47 adjusts the degree of opening of the emission opening of the irradiation field limiter 23. Furthermore, the control unit 47 controls the operation of the speaker 24.

For example, as illustrated in FIG. 7, in a case in which the operator turns on the first switch 25, the irradiation switch 17 outputs a warm-up command signal 55 to the radiation source control device 16. In a case in which the radiation source control device 16 receives the warm-up command signal 55, the radiation source control device 16 (control unit 47) performs a warm-up operation. The warm-up operation is an operation that preheats the filament and starts the rotation of the target. The radiation source control device 16 completes the warm-up operation in a case in which the filament reaches a predetermined temperature and the rotation speed of the target reaches a predetermined value. In addition, in a case in which the warm-up operation is completed, the beep sound 59 may be output from the speaker 24 to notify the operator that the warm-up operation has been completed.

For example, as illustrated in FIG. 8, in a case in which the operator turns on the second switch 26 in a state in which the warm-up operation is completed, the irradiation switch 17 outputs an irradiation start command signal 56 instructing the start of the emission of the radiation R to the radiation source control device 16. In a case in which the irradiation start command signal 56 is received, the radiation source control device 16 (control unit 47) transmits an irradiation start command reception signal 57 indicating that the irradiation start command signal 56 has been received as the synchronizing signal 60 to the signal relay device 14 and thus the electronic cassette 12.

For example, as illustrated in FIG. 9, after receiving the irradiation start command reception signal 57 from the radiation source control device 16, the electronic cassette 12 transmits an irradiation permission signal 58 for permitting the emission of the radiation R as the synchronizing signal 60 to the signal relay device 14 and thus the radiation source control device 16. In a case in which the irradiation permission signal 58 is received, the radiation source control device 16 (control unit 47) performs an irradiation operation indicated by the following procedure. First, the beep sound 59 is output from the speaker 24. Then, the tube voltage generator 48 applies the tube voltage to the radiation tube 22 to generate the radiation R from the radiation tube 22. At this time, a timer is operated to measure the time elapsed since the start of the generation of the radiation R. In a case in which the elapsed time reaches the irradiation time set in the irradiation conditions 37, the application of the tube voltage is stopped, and the emission of the radiation R is ended.

For example, as illustrated in FIG. 10, the electronic cassette 12 has a housing 65 with a flat box shape (a rectangular shape in a plan view). The housing 65 is made of conductive metal or resin. Therefore, the housing 65 also functions as an electromagnetic shield that prevents electromagnetic noise from entering the electronic cassette 12 and electromagnetic noise from being emitted from the electronic cassette 12 to the outside. A radiation transmission plate 66 having a rectangular plate shape which is slightly smaller than the housing 65 is attached to a front surface of the housing 65 on which the radiation R is incident. The radiation transmission plate 66 is made of, for example, a carbon material that is lightweight and has high rigidity and high radiation transparency.

An image output unit 67 is accommodated in the housing 65. The image output unit 67 has the detection panel 68 and a circuit unit 69. The detection panel 68 is composed of a scintillator 70 and the light detection substrate 71 which have substantially the same size as the radiation transmission plate 66.

The scintillator 70 and the light detection substrate 71 are stacked in the order of the scintillator 70 and the light detection substrate 71 as viewed from the front side of the housing 65 on which the radiation R is incident. The scintillator 70 has a phosphor, such as CsI:Tl (thallium-activated cesium iodide) or GOS ($Gd_2O_2S$:Tb, terbium-activated gadolinium oxysulfide), converts the incident radiation R into visible light, and emits the visible light. The light detection substrate 71 has a configuration in which a plurality of pixels 80 (see FIG. 12) are arranged on a single thin film transistor (TFT) active matrix substrate, detects the visible light emitted from the scintillator 70, and converts the visible light into an electric signal. The circuit unit 69 controls the operation of the pixels 80 of the light detection substrate 71 and generates the radiographic image 40 on the basis of the electric signal output from the light detection substrate 71.

Further, the scintillator 70 and the light detection substrate 71 may be stacked in the order of the light detection substrate 71 and the scintillator 70 as viewed from the front side. Furthermore, the detection panel 68 may not be an indirect conversion type in which the scintillator 70 converts the radiation R into visible light and the light detection substrate 71 converts the visible light into an electric signal as in this example, but may be a direct conversion type that directly converts the radiation R into an electric signal.

In addition, a battery and an antenna are provided in the housing 65, which is not illustrated. In a case in which wireless communication with, for example, the console 13 is performed by the antenna, the electronic cassette 12 can be driven by power from the battery and used wirelessly.

For example, as illustrated in FIG. 11, a length SSL of a short side 75 of the housing 65 is, for example, 431.8 mm (≈17 inches). In contrast, a length LSL of a long side 76 of the housing 65 is, for example, 787.4 mm (≈31 inches). That is, the length LSL of the long side 76 is larger than 431.8 mm.

For example, as illustrated in FIG. 12, the light detection substrate 71 has a configuration in which a plurality of pixels 80 are arranged in a two-dimensional matrix along X and Y directions which are orthogonal to each other. The X direction is a direction along the short side 75 and the Y direction is a direction along the long side 76. In a case in which the number of pixels 80 arranged in the X direction is M and the number of pixels 80 arranged in the Y direction is N, each of M and N is an integer equal to or greater than 2. For example, M is 2000, and N is 3800. As is well known, the pixel 80 includes a photoelectric conversion unit 81 that generates charge (electron-hole pair) by the incidence of visible light and accumulates the charge and a TFT 82 as a switching element that controls the accumulation of the charge in the photoelectric conversion unit 81 and the reading of the charge from the photoelectric conversion unit 81. The photoelectric conversion unit 81 includes, for example, a p-intrinsic-n (PIN) semiconductor layer, an upper electrode that is disposed above the semiconductor layer, and a lower electrode that is disposed below the semiconductor layer. A bias voltage is applied to the upper electrode. The lower electrode is connected to a drain electrode of the TFT 82.

N scanning lines 83 that extend in parallel to the X direction and M signal lines 84 that extend in parallel to the Y direction are formed on the light detection substrate 71. The N scanning lines 83 and the M signal lines 84 are wired in a grid shape. The pixel 80 is disposed in an intersection portion of the scanning line 83 and the signal line 84. Specifically, in the pixel 80, a gate electrode of the TFT 82 is connected to the scanning line 83, and a source electrode of the TFT 82 is connected to the signal line 84. Each scanning line 83 is commonly connected to M pixels 80 corresponding to one row along the X direction. Each signal line 84 is commonly connected to N pixels 80 corresponding to one column along the Y direction.

The circuit unit 69 has a gate driver 85 and a signal processing circuit 86. The scanning lines 83 are connected to the gate driver 85. The signal lines 84 are connected to the signal processing circuit 86.

The gate driver 85 outputs a gate pulse to the scanning line 83. The gate pulse is uniformly applied to the gate electrodes of all of the TFTs 82 of the M pixels 80 connected to the scanning line 83. The TFT 82 is turned on in a case in which the voltage of the gate pulse is at a high level and is turned off in a case in which the voltage is at a low level. The time when the TFT 82 is turned on is defined by the width of the gate pulse. The charge accumulated in the photoelectric conversion unit 81 of the pixel 80 is input to the signal processing circuit 86 through the signal line 84 in a case in which the TFT 82 is turned on.

The signal processing circuit 86 has a charge amplifier 90, an amplifier 91, a correlated double sampling (CDS) circuit (abbreviated to CDS in FIG. 12) 92, a multiplexer 93, and an analog/digital (A/D) converter 94. One charge amplifier 90, one amplifier 91, and one CDS circuit 92 are provided for each signal line 84. That is, M charge amplifiers 90, M amplifiers 91, and M CDS circuits 92 are provided.

The charge amplifier 90 integrates the charge input from the signal line 84, converts the integrated value into an analog voltage signal, and outputs the analog voltage signal. The charge amplifier 90 is composed of an operational amplifier 95, a capacitor 96, and a reset switch 97. The capacitor 96 and the reset switch 97 are connected in parallel between an input terminal and an output terminal of the operational amplifier 95. The signal line 84 is connected to the input terminal of the operational amplifier 95, and the amplifier 91 is connected to the output terminal of the operational amplifier 95.

The output terminal of the operational amplifier 95 in each column is connected to an input side of the multiplexer 93 through the amplifier 91 and the CDS circuit 92. The A/D converter 94 is connected to an output side of the multiplexer 93. The amplifier 91 amplifies the analog voltage signal with a predetermined amplification factor. The CDS circuit 92 performs well-known correlated double sampling on the amplified analog voltage signal to remove a reset noise component by the reset switch 97. In addition, the amplifier 91 is not limited to the configuration in which it is provided between the charge amplifier 90 and the CDS circuit 92. For example, the amplifier 91 may be provided between the CDS circuit 92 and the A/D converter 94, such as between the CDS circuit 92 and the multiplexer 93.

The multiplexer 93 sequentially selects the connected M CDS circuits 92 to sequentially input the analog voltage signals subjected to the correlated double sampling to the A/D converter 94. The A/D converter 94 sequentially converts the analog voltage signals input from the multiplexer 93 into digital signals and outputs the converted digital signals to a CPU 100. The CPU 100 has an image memory (not illustrated) corresponding to one frame and stores a digital signal based on the charge accumulated in the photoelectric conversion unit 81 of each pixel 80 as the radiographic image 40.

The CPU 100 controls the overall operation of the electronic cassette 12. The CPU 100 controls the operation of the circuit unit 69 such that the light detection substrate 71 performs any one of the accumulation operation, the image detection operation, or the charge reading operation and the radiographic image 40 is output from the light detection substrate 71. The CPU 100 is an example of a "processor" according to the technology of the present disclosure.

The accumulation operation is an operation that accumulates charge corresponding to the incident amount of radiation R in the photoelectric conversion unit 81. In the accumulation operation, the CPU 100 does not input the gate pulse from the gate driver 85 to the TFTs 82 and turns off the TFTs 82. Charge is accumulated in the photoelectric conversion unit 81 while the TFT 82 is in the off state.

The image detection operation is an operation that detects a digital signal based on the charge accumulated in the photoelectric conversion unit 81 in the accumulation operation as the radiographic image 40. In the image detection operation, the CPU 100 directs the gate driver 85 to sequentially generate the gate pulses for turning on the TFTs 82 in the same row at once, thereby sequentially activating the scanning lines 83 row by row. In a case in which the TFTs 82 corresponding to one row are turned on, the charge accumulated in each of the photoelectric conversion units 81 of the pixels 80 corresponding to one row is input to the signal processing circuit 86 through the signal line 84 in each column. As described above, in the signal processing circuit 86, the charge corresponding to one row is converted into an analog voltage signal by the charge amplifier 90, and the analog voltage signal is converted into a digital signal by the A/D converter 94.

In a case in which the charge amplifiers 90 output the analog voltage signals corresponding to one row, the CPU 100 turns on the reset switches 97. This resets the charge accumulated in the capacitors 96. After resetting the charge amplifiers 90 in this manner, the CPU 100 directs the gate driver 85 to output the gate pulse to the scanning line 83 in the next row such that the charge accumulated in the photoelectric conversion units 81 of the pixels 80 in the next row is input to the signal processing circuit 86. The CPU 100 directs the light detection substrate 71 to repeat this operation, thereby converting the charge accumulated in the photoelectric conversion units 81 of the pixels 80 in all rows into digital signals.

The charge reading operation is an operation that reads unnecessary charge, such as dark charge generated regardless of whether the radiation R is emitted and residual charge caused by the previous radiography, from the photoelectric conversion unit 81. In this example, the CPU 100 performs the charge reading operation using a sequential reading method which reads unnecessary charge row by row as in the above-mentioned image detection operation. Specifically, the CPU 100 directs the gate driver 85 to sequentially generate the gate pulse in each scanning line 83 row by row, thereby sequentially turning on the TFTs 82 row by row. Then, unnecessary charge accumulated in the photoelectric conversion unit 81 is input to the signal processing circuit 86 through the signal line 84.

The CPU 100 turns on the reset switch 97 of the charge amplifier 90 in synchronization with the generation of the gate pulse to reset the unnecessary charge. As described above, in the charge reading operation, unlike the image detection operation, the conversion of charge into an analog voltage signal and the conversion of the analog voltage signal into a digital signal are not performed. Of course, in order to acquire an offset correction image or a residual image correction image which will be described below, the conversion of charge into an analog voltage signal and the conversion of the analog voltage signal into a digital signal may be performed in the charge reading operation as in the image detection operation.

The charge reading operation from the start of the reading of unnecessary charge in the first row, which is an initial row, to the end of the reading of unnecessary charge in an N-th row, which is the last row, is counted as one operation.

The CPU 100 performs various correction processes on the radiographic image 40. The various correction processes include, for example, an offset correction process, a residual image correction process, a sensitivity correction process, and a defective pixel correction process. The offset correction process is a process that subtracts the offset correction image detected in a state in which the radiation R is not emitted from the radiographic image 40 in units of pixels. The CPU 100 performs the offset correction process to remove fixed pattern noise caused by, for example, dark charge from the radiographic image 40. The residual image correction process is a process that subtracts a residual image correction image corresponding to the residual charge caused by the previous radiography from the radiographic image 40 in units of pixels. The sensitivity correction process is a process that corrects, for example, a variation in the sensitivity of the photoelectric conversion unit 81 in each pixel 80 and a variation in the output characteristics of the signal processing circuit 86 on the basis of sensitivity correction data. The defective pixel correction process is a process that linearly interpolates the value of a defective pixel with the values of surrounding normal pixels 80 on the basis of the information of the defective pixel having an abnormal value, which is generated during shipping or a regular inspection. In addition, the various correction processes may be performed in the console 13.

A storage 101, a memory 102 and a communication I/F 103 are connected to the CPU 100. The CPU 100, the storage 101, the memory 102, and the communication I/F 103 are connected to each other through a bus line (not illustrated). The CPU 100, the storage 101, and the memory 102 are an example of a "computer" according to the technology of the present disclosure.

An operation program 104 is stored in the storage 101. The CPU 100 loads the operation program 104 to the memory 102 and performs a process corresponding to the operation program 104. Therefore, the CPU 100 controls the overall operation of each unit of the electronic cassette 12. In addition, the memory 102 may be provided in the CPU 100. The operation program 104 is an example of a "program for operating a radiographic image detector" according to the technology of the present disclosure.

The communication I/F 103 is connected to the console 13 and the signal relay device 14 wirelessly or in a wired manner such that it can communicate with the console 13 and the signal relay device 14. The communication I/F 103 transmits and receives the setting notification signal 39 and the radiographic image 40 to and from console 13. In addition, the communication I/F 103 transmits and receives the synchronizing signal 60 to and from signal relay device 14.

For example, as illustrated in FIG. 13, in a case in which the operation program 104 is started, the CPU 100 functions as a setting notification signal receiving unit 110, an operation control unit 111, a notification unit 112, a synchronizing signal transmitting and receiving unit 113, a correction processing unit 114, and an image transmission unit 115.

The setting notification signal receiving unit 110 receives the setting notification signal 39 from the console 13. The setting notification signal receiving unit 110 outputs, to operation control unit 111, information indicating that the setting notification signal 39 has been received and the accumulation time included in the setting notification signal 39.

The operation control unit 111 controls the operation of the circuit unit 69. In a case in which the information indicating that the setting notification signal 39 has been received is input from the setting notification signal receiving unit 110, the operation control unit 111 operates the circuit unit 69 to return the light detection substrate 71 and the like from a standby state to a normal use state. The standby state is a state in which power is supplied only to the minimum functions, such as the function of communicating with the console 13 through the communication I/F 103, and other functions are suspended. On the other hand, the normal use state is a state in which power is supplied to all of the functions and the light detection substrate 71 can detect the radiographic image 40.

After returning the light detection substrate 71 and the like to the normal use state, the operation control unit 111 directs the light detection substrate 71 to perform the charge reading operation a predetermined number of times. A sufficient number of times (for example, 10 times) to remove unnecessary charge from the photoelectric conversion unit 81 is set as the predetermined number of times. After completing the predetermined number of charge reading operations, the operation control unit 111 outputs, to the notification unit 112, information indicating that the predetermined number of charge reading operations have been completed.

In a case in which the information indicating that the predetermined number of charge reading operations has been completed is received from the operation control unit 111, the notification unit 112 transmits an imaging preparation completion signal 120 to the console 13. The imaging preparation completion signal 120 is a signal indicating that the predetermined number of charge reading operations have been completed and the electronic cassette 12 is ready for radiography.

The synchronizing signal transmitting and receiving unit 113 transmits and receives the synchronizing signal 60 to and from the signal relay device 14 and thus the radiation source control device 16. Specifically, the synchronizing signal transmitting and receiving unit 113 receives the irradiation start command reception signal 57 from the radiation source control device 16. The synchronizing signal transmitting and receiving unit 113 outputs, to the operation control unit 111, that the irradiation start command reception signal 57 has been received.

The operation control unit 111 directs the light detection substrate 71 to continue the charge reading operation even after the predetermined number of charge reading operations have been completed. The operation control unit 111 directs the light detection substrate 71 to start the accumulation operation in a case in which the information indicating that the irradiation start command reception signal 57 has been received is input from the synchronizing signal transmitting and receiving unit 113. The operation control unit 111 outputs, to the synchronizing signal transmitting and receiving unit 113, information indicating that the light detection substrate 71 has been directed to start the accumulation operation. The synchronizing signal transmitting and receiving unit 113 transmits the irradiation permission signal 58 to the radiation source control device 16 in a case in which the information indicating that the light detection substrate 71 has been directed to start the accumulation operation is input from the operation control unit 111.

The operation control unit 111 measures the time elapsed since the start of the accumulation operation. In a case in which the elapsed time reaches the accumulation time included in the setting notification signal 39, the operation control unit 111 directs the light detection substrate 71 to perform the image detection operation. Then, the radiographic image 40 is output from the signal processing circuit 86.

The correction processing unit 114 performs various correction processes including the above-described offset correction process on the radiographic image 40 from the signal processing circuit 86. The correction processing unit 114 outputs the radiographic image 40 subjected to the correction processes to the image transmission unit 115. The image transmission unit 115 transmits the radiographic image 40 to the console 13.

In a case in which the imaging preparation completion signal 120 is received from the electronic cassette 12, the CPU 32 of the console 13 displays, for example, a notification screen 130 illustrated in FIG. 14 on the display 20. A message 131 indicating that the predetermined number of charge reading operations have been completed and the electronic cassette 12 is ready for radiography is displayed on the notification screen 130. An OK button 132 is operated to make the notification screen 130 disappear.

FIG. 15 is a timing chart illustrating a series of operations of the console 13, the radiation source control device 16, and the electronic cassette 12 (light detection substrate 71) in one radiography operation. First, in a case in which the operator sets the irradiation conditions 37 in the console 13, the console 13 transmits the setting notification signal 39 to the electronic cassette 12. In a case in which the electronic cassette 12 receives the setting notification signal 39, it returns from the standby state to the normal use state. Then, the light detection substrate 71 of the electronic cassette 12 starts the charge reading operation.

In a case in which the predetermined number of charge reading operations have been completed, the electronic cassette 12 transmits the imaging preparation completion signal 120 to the console 13. The console 13 displays the notification screen 130 on the display 20 in a case in which the imaging preparation completion signal 120 is received.

In a case in which the operator turns on the first switch 25 of the irradiation switch 17, the radiation source control device 16 performs the warm-up operation. Then, in a case in which the operator turns on the second switch 26 of the irradiation switch 17, the radiation source control device 16 transmits the irradiation start command reception signal 57 to the electronic cassette 12. The light detection substrate 71 continues the charge reading operation. The light detection substrate 71 starts the accumulation operation in a case in which the irradiation start command reception signal 57 is received. In addition, the electronic cassette 12 transmits the irradiation permission signal 58 to the radiation source control device 16. The radiation source control device 16 performs the irradiation operation in a case in which the irradiation permission signal 58 is received.

In a case in which the time elapsed since the start of the accumulation operation reaches the accumulation time included in the setting notification signal 39, the light detection substrate 71 performs the image detection operation and outputs the radiographic image 40. The electronic cassette 12 transmits the radiographic image 40 to the console 13. Then, the electronic cassette 12 returns to the standby state. The console 13 displays the radiographic image 40 on the display 20.

Next, the operation of the above-mentioned configuration will be described with reference to a flowchart illustrated in FIG. 16. In a case in which the power of the electronic cassette 12 is turned on, the operation program 104 is started. Then, the CPU 100 of the electronic cassette 12 functions as the setting notification signal receiving unit 110, the operation control unit 111, the notification unit 112, the synchronizing signal transmitting and receiving unit 113, the correction processing unit 114, and the image transmission unit 115 as illustrated in FIG. 13.

First, the operator sets the irradiation conditions 37 in the console 13. Then, the setting notification signal 39 is transmitted from the console 13 to the electronic cassette 12.

In the electronic cassette 12, the setting notification signal receiving unit 110 receives the setting notification signal 39 from the console 13 (YES in Step ST100). Information indicating that the setting notification signal 39 has been received and the accumulation time included in the setting notification signal 39 are output from the setting notification signal receiving unit 110 to the operation control unit 111.

The operation control unit 111 returns the light detection substrate 71 and the like from the standby state to the normal use state (Step ST110). Then, the light detection substrate 71 performs the charge reading operation under the control of the operation control unit 111 (Step ST120). The charge reading operation is continued a predetermined number of times.

After the predetermined number of charge reading operations are completed (YES in Step ST130), the operation control unit 111 outputs, to the notification unit 112, information indicating that the predetermined number of charge reading operations have been completed. Then, the imaging preparation completion signal 120 is transmitted from the notification unit 112 to the console 13 (Step ST140). Then, the charge reading operation is continued.

The notification screen 130 is displayed on the display 20 in the console 13 that has received the imaging preparation completion signal 120. In this way, the operator is notified that the predetermined number of charge reading operations have been completed and that the electronic cassette 12 is ready for radiography.

After setting the irradiation conditions 37, the operator adjusts the positions of the electronic cassette 12, the radiation source 15, and the subject H to prepare for radiography. Then, the operator turns on the first switch 25 of the irradiation switch 17 to direct the radiation source control device 16 to perform the warm-up operation. Then, the operator turns on the second switch 26 of the irradiation switch 17. Then, the irradiation start command reception signal 57 is transmitted from the radiation source control device 16 to the electronic cassette 12.

In the electronic cassette 12, the synchronizing signal transmitting and receiving unit 113 receives the irradiation start command reception signal 57 from the radiation source control device 16 (YES in Step ST160). Then, information indicating that the irradiation start command reception signal 57 has been received is output from the synchronizing signal transmitting and receiving unit 113 to the operation control unit 111.

The light detection substrate 71 performs the accumulation operation under the control of the operation control unit 111. Further, the synchronizing signal transmitting and receiving unit 113 transmits the irradiation permission signal 58 to the radiation source control device 16 (Step ST170).

The radiation source control device 16 that has received the irradiation permission signal 58 performs the irradiation operation to irradiate the subject H with the radiation R. The scintillator 70 converts the radiation R transmitted through the subject H into visible light. The visible light is incident on the light detection substrate 71. Since the accumulation operation is performed in the light detection substrate 71, charge corresponding to the incident visible light is accumulated in the photoelectric conversion unit 81 of each pixel 80.

The operation control unit 111 measures the time elapsed since the start of the accumulation operation. In a case in which the elapsed time reaches the accumulation time (YES in Step ST180), the image detection operation is performed in the light detection substrate 71 under the control of the operation control unit 111 (Step ST190). Therefore, the radiographic image 40 is output from the signal processing circuit 86.

The correction processing unit 114 performs various correction processes on the radiographic image 40, and the image transmission unit 115 transmits the radiographic image 40 to the console 13 (Step ST200). Then, the operation control unit 111 returns the light detection substrate 71 and the like to the standby state (Step ST210), and the process is ended. In addition, even in a case in which a predetermined time has elapsed since the reception of the setting notification signal 39 by the setting notification signal receiving unit 110 after the transmission of the imaging preparation completion signal 120 (YES in Step ST150), the operation control unit 111 determines that a time-out has occurred, and the light detection substrate 71 and the like are returned to the standby state (Step ST210). Then, the process is ended.

The console 13 performs various types of image processing on the radiographic image 40 from the electronic cassette 12. Then, the radiographic image 40 is displayed on the display 20.

As described above, the electronic cassette 12 has the detection panel 68 (light detection substrate 71) in which the pixels 80 accumulating charge corresponding to the radiation R emitted from the radiation source 15 are arranged. The CPU 100 of the electronic cassette 12 functions as the setting notification signal receiving unit 110, the operation control unit 111, the notification unit 112, and the synchronizing signal transmitting and receiving unit 113. The synchronizing signal transmitting and receiving unit 113 transmits and receives the synchronizing signal 60 to and from the radiation source control device 16. The setting notification signal receiving unit 110 receives the setting notification signal 39 indicating that the irradiation conditions 37 have been set from the console 13. After receiving the setting notification signal 39, the operation control unit 111 directs the light detection substrate 71 to start the charge reading operation. The notification unit 112 transmits the imaging preparation completion signal 120 to the console 13 after the predetermined number of charge reading operations are completed to notify that the predetermined number of charge reading operations have been completed. Therefore, the operator is prevented from giving an instruction to start the emission of the radiation R before the predetermined number of charge reading operations are completed. As a result, the possibility that the emission of the radiation R will be started after the predetermined number of charge reading operations are completed is reduced. Therefore, it is possible to reduce the concern that the operator will feel uncomfortable.

The following is considered: the light detection substrate 71 performs the charge reading operation not after the irradiation conditions 37 are set and the setting notification signal 39 is received, but in a case in which the operator turns on the first switch 25 of the irradiation switch 17, as in a comparative example illustrated in FIG. 17. In a case in which the operator turns on the second switch 26 of the irradiation switch 17, a situation in which the predetermined number of charge reading operations have not yet been completed occurs. Then, a waiting time WT until the predetermined number of charge reading operations are completed, the irradiation permission signal 58 is transmitted and received between the electronic cassette 12 and the radiation source control device 16, and the radiation source control device 16 starts the irradiation operation (start the emission of the radiation R) after the second switch 26 is turned on is required. There is a concern that the waiting time WT will make the operator feel uncomfortable. In the technology of the present disclosure, in a case in which the operator turns on the second switch 26, the predetermined number of charge reading operations have already been completed. Therefore, the waiting time WT does not occur.

As the time required for the predetermined number of charge reading operations becomes longer, the waiting time WT becomes longer. The time required for one charge reading operation becomes longer as the number of rows of pixels 80 becomes larger. Therefore, in the case of the electronic cassette 12 in which the length of the long side 76 is larger than 431.8 mm as in this example, the waiting time WT is longer than that in the case of the electronic cassette in which the length of the long side 76 is equal to or less than 431.8 mm. Therefore, according to the electronic cassette 12 in which the length of the long side 76 is larger than 431.8 mm, it is possible to further exhibit the effect of reducing the concern that the operator will feel uncomfortable. In addition, in a case in which the length of the long side 76 is 431.8 mm, the time required for the predetermined number of charge reading operations is, for example, about 1 second. However, in a case in which the length of the long side 76 is 787.4 mm as in this example, the time required for the predetermined number of charge reading operations is as long as, for example, about 2 seconds.

The radiation source control device 16 receives the irradiation start command signal 56 for instructing the radiation source 15 to start the emission of the radiation R and transmits the irradiation start command reception signal 57 indicating that the irradiation start command signal 56 has been received as the synchronizing signal 60. The operation control unit 111 directs the light detection substrate 71 to continue the charge reading operation until the synchronizing signal transmitting and receiving unit 113 receives the irradiation start command reception signal 57 from the radiation source control device 16 even after the predetermined number of charge reading operations are completed. Therefore, it is possible to remove the unnecessary charge generated after the predetermined number of charge reading operations are completed.

The operation control unit 111 directs the light detection substrate 71 to start the accumulation operation after receiving the irradiation start command reception signal 57 from the radiation source control device 16. The synchronizing signal transmitting and receiving unit 113 transmits the irradiation permission signal 58 permitting the emission of the radiation R to the radiation source control device 16. Therefore, it is possible to synchronize the irradiation operation of the radiation source control device 16 with the accumulation operation of the light detection substrate 71.

In this example, the imaging-related information is the irradiation conditions 37 of the radiation R. The timing when the irradiation conditions 37 are set is before an instruction to start the emission of the radiation R is input to the radiation source 15. Therefore, in a case in which the irradiation conditions 37 are set and then the predetermined number of charge reading operations are started, the probability that the predetermined number of charge reading operations will have already been completed at the time when the radiation source 15 is instructed to start the emission of the radiation R is very high. Therefore, the chances of starting the emission of the radiation R after waiting for the completion of the predetermined number of charge reading operations are greatly reduced, and it is possible to further reduce the concern that the operator will feel discomfort.

Further, in addition to or instead of the irradiation conditions 37 given as an example, the imaging-related information may include at least one of the accumulation time, the imaging part of the subject H, the imaging posture of the subject H, or the imaging direction of the subject H.

Second Embodiment

For example, as illustrated in FIG. 18, a plurality of radiation detection pixels 80X are discretely provided on a light detection substrate 140 according to this embodiment. The radiation detection pixel 80X has the same basic configuration as the pixel 80 in that it has a photoelectric conversion unit 81 and a TFT 82, but is different from the pixel 80 in that a source electrode and a drain electrode of the TFT 82 are short-circuited. Therefore, charge generated in the photoelectric conversion unit 81 of the radiation detection pixel 80X is always input to the signal processing circuit 86 through the signal line 84 regardless of the operating state of the TFT 82.

The signal processing circuit 86 outputs a digital signal (hereinafter, referred to as a radiation detection signal 141 (see FIG. 19)) based on the charge generated in the photoelectric conversion unit 81 of the radiation detection pixel 80X to a CPU 142 at a sample interval of, for example, microsecond order. The radiation detection signal 141 can be output to the CPU 142 even while the light detection substrate 140 is performing the charge reading operation or the accumulation operation. During the charge reading operation, the radiation detection signal 141 is output by accumulating charge in the capacitor 96 without turning on the reset switch 97 of the charge amplifier 90 in the column in which the radiation detection pixel 80X is present. The level of the radiation detection signal 141 changes according to the irradiation dose of the radiation R per unit time. In a case in which the emission of the radiation R is started, the irradiation dose of the radiation R per unit time gradually increases. Therefore, the level of the radiation detection signal 141 also gradually increases.

An operation program 143 is stored in the storage 101. The operation program 143 is an example of a "program for operating a radiographic image detector" according to the technology of the present disclosure. In a case in which the operation program 143 is started, the CPU 142 functions as a detection unit 145 in addition to each of the processing units 110 to 115 (only the operation control unit 111 is illustrated in FIG. 19) according to the first embodiment as illustrated in FIG. 19 as an example.

The radiation detection signal 141 is input from the signal processing circuit 86 to the detection unit 145. The detection unit 145 compares the level of the radiation detection signal 141 with a preset irradiation start detection threshold value. In a case in which the level of the radiation detection signal 141 is equal to or greater than the irradiation start detection threshold value, the detection unit 145 determines that the radiation source 15 has started the emission of the radiation R and detects the start of the emission of the radiation R. The detection unit 145 outputs, to the operation control unit 111, information indicating that the start of the emission of the radiation R has been detected. The operation control unit 111 directs the light detection substrate 140 to start the accumulation operation in a case in which the information indicating that the start of the emission of the radiation R has been detected is input from the detection unit 145. According to the radiation detection pixel 80X and the detection unit 145, the electronic cassette can synchronize the start of the emission of the radiation R with the start of the accumulation operation, without transmitting and receiving the synchronizing signal 60 to and from the radiation source control device. The radiation detection pixel 80X and the detection unit 145 are an example of "a function of detecting the start of the emission of radiation without depending on a synchronizing signal" according to the technology of the present disclosure.

For example, as illustrated in FIG. 20, in the electronic cassette according to this embodiment, as in the first embodiment, after the setting notification signal 39 indicating that the irradiation conditions 37 have been set is received, the light detection substrate 140 starts the predetermined number of charge reading operations. Further, after the predetermined number of charge reading operations are completed, the imaging preparation completion signal 120 indicating that the predetermined number of charge reading operations have been completed is transmitted to the console 13. Furthermore, in a case in which the accumulation time included in the setting notification signal 39 has elapsed since the start of the accumulation operation, the light detection substrate 140 starts the image detection operation. The difference from the first embodiment is that, instead of transmitting and receiving the synchronizing signal 60 (the irradiation start command reception signal 57 and the irradiation permission signal 58) to and from the radiation source control device, the detection unit 145 detects the start of the emission of the radiation R and the light detection substrate 140 starts the accumulation operation according to the detection of the start of the emission.

As described above, in the second embodiment, the electronic cassette has a function of detecting the start of the emission of the radiation R, without depending on the synchronizing signal 60. Therefore, it is possible to respond to a radiation source control device that does not have a function of transmitting and receiving the synchronizing signal 60. In addition, the following aspect is the same as that in the first embodiment: after the setting notification signal 39 indicating that the irradiation conditions 37 have been set is received, the light detection substrate 140 starts the predetermined number of charge reading operations; and, after the predetermined number of charge reading operations are completed, the imaging preparation completion signal 120 indicating that the predetermined number of charge reading operations have been completed is transmitted to the console 13. Therefore, even in the second embodiment, it is possible to obtain the effect of reducing the concern that the operator will feel discomfort.

In addition, in a case in which the emission of the radiation R is ended, the level of the radiation detection signal 141 gradually decreases and finally becomes zero. Therefore, the detection unit 145 may detect not only the start of the emission of the radiation R but also the end of the emission. Specifically, the detection unit 145 compares the level of the radiation detection signal 141 with a preset irradiation end detection threshold value. In a case in which the level of the radiation detection signal 141 is less than the irradiation end detection threshold value, the detection unit 145 determines that the emission of the radiation R by the radiation source 15 has ended and detects the end of the emission of the radiation R. The detection unit 145 outputs, to the operation control unit 111, information indicating that the end of the emission of the radiation R has been detected. The operation control unit 111 directs the light detection substrate 140 to perform the image detection operation in a case in which the information indicating that the end of the emission of the radiation R has been detected is input from the detection unit 145. In this way, the electronic cassette can synchronize not only the start of the emission of the radiation R and the start of the accumulation operation but also the end of the emission of the radiation R and the end of the accumulation operation (the start of the image detection operation).

The radiation detection pixel 80X may have a configuration in which only the photoelectric conversion unit 81 is provided, the TFT 82 is not provided, and the photoelectric conversion unit 81 is directly connected to the signal line 84. In addition, the radiation detection pixel 80X has exactly the same configuration as the pixel 80 without short-circuiting the source electrode and the drain electrode of the TFT 82, and a dedicated gate driver may be provided for the radiation detection pixel 80X such that charge can be read from the radiation detection pixel 80X independently of the pixel 80.

In the first embodiment, the notification screen 130 is displayed on the display 20 of the console 13 to notify the operator that the predetermined number of charge reading operations have been completed. However, the present disclosure is not limited thereto. An indicator, such as a light emitting diode (LED), may be provided in the housing 65 of the electronic cassette 12, and the operator may be notified that the predetermined number of charge reading operations have been completed through the indicator. Further, the operator may be notified that the predetermined number of charge reading operations have been completed through the speaker 24 of the radiation source control device 16. Alternatively, a warning light may be provided in the upright imaging stand 18 and turned on to notify the operator that the predetermined number of charge reading operations have been completed.

In the first embodiment, the electronic cassette 12 in which the length of the long side 76 is larger than 431.8 mm is given as an example. However, the present disclosure is not limited thereto. An electronic cassette in which the length of one side is less than 431.8 mm may be used.

In each of the above-described embodiments, the emission of the radiation R is ended on the basis of the irradiation time set in the irradiation conditions 37. However, the present disclosure is not limited thereto. The emission of the radiation R may be ended by an auto exposure control (AEC) function. The AEC function is a function that detects the dose of the radiation R during the emission of the radiation R and stops the emission of the radiation R at the time when an integrated value of the detected dose (cumulative dose) reaches a preset target dose. In this case, in the electronic cassette, the detection panel starts the image detection operation in a case in which the cumulative dose of the radiation R reaches the target dose.

The electronic cassette is given as an example of the radiographic image detector. However, the present disclosure is not limited thereto. A radiographic image detector that is installed in the imaging table may also be used. Alternatively, a radiographic image detector that is fixed at a position facing the radiation source in a C-arm or the like may be used.

In each of the above-described embodiments, for example, the following various processors can be used as a hardware structure of processing units performing various processes, such as the setting notification signal receiving unit 110, the operation control unit 111, the notification unit 112, the synchronizing signal transmitting and receiving unit 113, the correction processing unit 114, the image transmission unit 115, and the detection unit 145. The various processors include, for example, the CPUs 100 and 142 which are general-purpose processors executing software (operation programs 104 and 143) to function as various processing units as described above, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of ASICs and/or a combination of an ASIC and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

Furthermore, specifically, an electric circuit (circuitry) obtained by combining circuit elements, such as semiconductor elements, can be used as the hardware structure of the various processors.

In the technology of the present disclosure, the above-described various embodiments and/or various modification examples may be combined with each other. In addition, the present disclosure is not limited to each of the above-described embodiments, and various configurations can be used without departing from the gist of the present disclosure. Furthermore, the technology of the present disclosure extends to a storage medium that non-temporarily stores a program, in addition to the program.

The above descriptions and illustrations are detailed descriptions of portions related to the technology of the present disclosure and are merely examples of the technology of the present disclosure. For example, the above description of the configurations, functions, operations, and effects is the description of examples of the configurations, functions, operations, and effects of portions according to the technology of the present disclosure. Therefore, unnecessary portions may be deleted or new elements may be added or replaced in the above descriptions and illustrations without departing from the gist of the technology of the present disclosure. In addition, in the content described and illustrated above, the description of, for example, common technical knowledge that does not need to be particularly described to enable the implementation of the technology of the present disclosure is omitted in order to avoid confusion and facilitate the understanding of portions related to the technology of the present disclosure.

In the specification, "A and/or B" is synonymous with "at least one of A or B". That is, "A and/or B" means only A, only B, or a combination of A and B. Further, in the specification, the same concept as "A and/or B" is applied to a case in which the connection of three or more matters is expressed by "and/or".

All of the documents, the patent applications, and the technical standards described in the specification are incorporated by reference herein to the same extent as each individual document, each patent application, and each technical standard are specifically and individually stated to be incorporated by reference.

What is claimed is:

1. A radiographic image detector having a detection panel in which pixels accumulating charge corresponding to radiation emitted from a radiation source are arranged, the radiographic image detector comprising:
   a processor,
   wherein the processor transmits and receives a synchronizing signal for synchronizing an operation of the radiation source to and from a radiation source control device which controls the operation of the radiation source,
   receives, from an imaging control device in which imaging-related information related to radiography is set, a setting notification signal indicating that the imaging-related information has been set,
   directs the detection panel to start a charge reading operation of reading the charge from the pixel after the setting notification signal is received, and
   notifies, after a predetermined number of charge reading operations are completed, that the predetermined number of charge reading operations have been completed.

2. The radiographic image detector according to claim 1, wherein the radiographic image detector has a rectangular shape in a plan view and has a long side with a length greater than 431.8 mm.

3. The radiographic image detector according to claim 1, wherein the radiation source control device receives an irradiation start command signal for instructing the radiation source to start the emission of the radiation and transmits an irradiation start command reception signal indicating that the irradiation start command signal has been received as the synchronizing signal, and
   the processor directs the detection panel to continue the charge reading operation until the irradiation start command reception signal is received from the radiation source control device even after the predetermined number of charge reading operations are completed.

4. The radiographic image detector according to claim 3, wherein, after receiving the irradiation start command reception signal from the radiation source control device, the processor directs the detection panel to start an accumulation operation of accumulating the charge in the pixel and transmits an irradiation permission signal for permitting the emission of the radiation to the radiation source control device.

5. The radiographic image detector according to claim 1, wherein the imaging-related information includes at least one of a time for which the detection panel performs an accumulation operation of accumulating the charge in the pixel, irradiation conditions of the radiation, an imaging part of a subject, an imaging posture of the subject, or an imaging direction of the subject.

6. The radiographic image detector according to claim 1, wherein the radiographic image detector has a function of detecting a start of the emission of the radiation without depending on the synchronizing signal.

7. A method for operating a radiographic image detector having a detection panel in which pixels accumulating charge corresponding to radiation emitted from a radiation source are arranged, the method comprising:
   transmitting and receiving a synchronizing signal for synchronizing an operation of the radiation source to and from a radiation source control device which controls the operation of the radiation source;
   receiving, from an imaging control device in which imaging-related information related to radiography is set, a setting notification signal indicating that the imaging-related information has been set;
   directing the detection panel to start a charge reading operation of reading the charge from the pixel after the setting notification signal is received; and
   notifying, after a predetermined number of charge reading operations are completed, that the predetermined number of charge reading operations have been completed.

8. A non-transitory computer-readable storage medium storing a program for operating a radiographic image detector having a detection panel in which pixels accumulating charge corresponding to radiation emitted from a radiation source are arranged, the program causing a computer to execute a process comprising:
   transmitting and receiving a synchronizing signal for synchronizing an operation of the radiation source to and from a radiation source control device which controls the operation of the radiation source;
   receiving, from an imaging control device in which imaging-related information related to radiography is set, a setting notification signal indicating that the imaging-related information has been set;
   directing the detection panel to start a charge reading operation of reading the charge from the pixel after the setting notification signal is received; and
   notifying, after a predetermined number of charge reading operations are completed, that the predetermined number of charge reading operations have been completed.

9. A radiography system comprising:
   a radiation source that emits radiation;
   a radiation source control device that controls an operation of the radiation source;
   a radiographic image detector that has a detection panel in which pixels accumulating charge corresponding to the radiation are arranged; and
   an imaging control device in which imaging-related information related to radiography is set,
   wherein the radiographic image detector has a processor, and
   the processor transmits and receives a synchronizing signal for synchronizing an operation of the radiation source to and from the radiation source control device,
   receives a setting notification signal indicating that the imaging-related information has been set from the imaging control device,
   directs the detection panel to start a charge reading operation of reading the charge from the pixel after the setting notification signal is received, and
   notifies, after a predetermined number of charge reading operations are completed, that the predetermined number of charge reading operations have been completed.

* * * * *